United States Patent
Carter et al.

(10) Patent No.: US 9,655,821 B2
(45) Date of Patent: *May 23, 2017

(54) PERSONAL CARE COMPOSITION COMPRISING A PRE-EMULSIFIED FORMULATION

(71) Applicant: The Procter & Gamble Company, Cincinnati, OH (US)

(72) Inventors: John David Carter, Mason, OH (US); Qing Stella, Cincinnati, OH (US); Eric Scott Johnson, Hamilton, OH (US); Michael Stephen Maile, Maineville, OH (US); Sean Michael Renock, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/245,254

(22) Filed: Apr. 4, 2014

(65) Prior Publication Data

US 2014/0309154 A1 Oct. 16, 2014

Related U.S. Application Data

(60) Provisional application No. 61/809,015, filed on Apr. 5, 2013.

(51) Int. Cl.
| | |
|---|---|
| *A61K 8/06* | (2006.01) |
| *A61K 8/37* | (2006.01) |
| *A61Q 5/02* | (2006.01) |
| *A61Q 19/10* | (2006.01) |
| *C11D 1/00* | (2006.01) |
| *C11D 1/02* | (2006.01) |
| *A61K 8/60* | (2006.01) |
| *A61K 8/44* | (2006.01) |
| *A61K 8/46* | (2006.01) |
| *A61K 8/49* | (2006.01) |

(52) U.S. Cl.
CPC ............... *A61K 8/06* (2013.01); *A61K 8/068* (2013.01); *A61K 8/37* (2013.01); *A61K 8/375* (2013.01); *A61K 8/44* (2013.01); *A61K 8/463* (2013.01); *A61K 8/466* (2013.01); *A61K 8/4973* (2013.01); *A61K 8/4993* (2013.01); *A61K 8/604* (2013.01); *A61Q 5/02* (2013.01); *A61Q 19/10* (2013.01); *A61K 2800/21* (2013.01); *A61K 2800/52* (2013.01)

(58) Field of Classification Search
CPC . A61K 8/06; A61K 8/068; A61K 8/37; A61K 8/604; A61K 8/466; A61K 8/4973; A61K 2800/21; A61Q 5/02; A61Q 19/10; C11D 1/00; C11D 1/02; C11D 3/2093
See application file for complete search history.

(56) References Cited

U.S. PATENT DOCUMENTS

| | | |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,809,971 A | 10/1957 | Bernstein |
| 2,826,551 A | 3/1958 | Geen |
| 3,236,733 A | 2/1966 | Karsten |
| 3,753,196 A | 8/1973 | Kurtz |
| 3,761,418 A | 9/1973 | Parran |
| 3,829,563 A | 8/1974 | Barry et al. |
| 3,912,665 A | 10/1975 | Spitzer et al. |
| 3,912,666 A | 10/1975 | Spitzer et al. |
| 3,929,678 A | 12/1975 | Laughlin |
| 3,964,500 A | 6/1976 | Drakoff |

(Continued)

FOREIGN PATENT DOCUMENTS

| | | |
|---|---|---|
| CN | 1579364 A | 2/2005 |
| CN | 1875915 A | 12/2006 |

(Continued)

OTHER PUBLICATIONS

Starch, "New Cosmetic Ingredients Based on Soybean Oil", IP.com Journal, IP.com Inc., West Henrietta, New York, pp. 1-15, dated Jun. 15, 2007.*
USPTO Office Action for U.S. Appl. No. 13/857,522 dated Oct. 24, 2015; 7 pages.
USPTO Office Action for U.S. Appl. No. 13/857,540 dated Oct. 24, 2015; 6 pages.
Crepaldi, EL, "Chemical, Structural, and Thermal Properties of Zn(II)—Cr(III) Layered Double Hydroxides Intercalated with Sulfated and Sulfonated Surfactants" *J. Colloid Interfac. Sci.* 2002, 248, 429-42.

(Continued)

*Primary Examiner* — Brian P Mruk
(74) *Attorney, Agent, or Firm* — Linda M. Sivik

(57) ABSTRACT

The present invention is directed to a personal care composition comprising a pre-emulsified emulsion comprising from about 0.25% to about 80% of one or more materials selected from the group comprising metathesized unsaturated polyol esters, sucrose polyesters, fatty esters with a molecular weight greater than or equal to 1500 and mixtures thereof or, by weight of said hair care composition; wherein an emulsifier is selected from the group consisting of anionic, non-ionic, cationic, amphoteric and mixtures thereof wherein the average particle size of the pre-emulsified emulsion is from about 20 nanometer to 20 microns; from about 5% to about 50% of one or more anionic surfactants, by weight of said hair care composition; at least about 20% of an aqueous carrier, by weight of said hair care composition wherein the composition is stable with respect to one of the following measures selected from emulsion particle size, viscosity or visual phase separation and mixtures thereof.

27 Claims, No Drawings

(56) References Cited

U.S. PATENT DOCUMENTS

| | | |
|---|---|---|
| 4,152,416 A | 5/1979 | Spitzer et al. |
| 4,197,865 A | 4/1980 | Jacquet |
| 4,217,914 A | 8/1980 | Jacquet |
| 4,275,055 A | 6/1981 | Nachtigal |
| 4,323,683 A | 4/1982 | Bolich, Jr. |
| 4,345,080 A | 8/1982 | Bolich, Jr. |
| 4,364,837 A | 12/1982 | Pader |
| 4,381,919 A | 5/1983 | Jacquet |
| 4,389,418 A | 6/1983 | Burton |
| 4,422,853 A | 12/1983 | Jacquet |
| 4,470,982 A | 9/1984 | Winkler |
| 4,472,291 A | 9/1984 | Rosano |
| 4,507,280 A | 3/1985 | Pohl |
| 4,529,586 A | 7/1985 | De Marco |
| 4,637,933 A | 1/1987 | Zabotto nee Arribau et al. |
| 4,663,158 A | 5/1987 | Wolfram |
| 4,673,526 A | 6/1987 | Zabotto et al. |
| 4,741,855 A | 5/1988 | Grote |
| 4,746,460 A | 5/1988 | Taylor |
| 4,774,016 A | 9/1988 | Gazzani |
| 4,897,214 A | 1/1990 | Gazzani |
| 4,997,641 A | 3/1991 | Hartnett et al. |
| 5,093,023 A | 3/1992 | Pantini et al. |
| 5,104,646 A | 4/1992 | Bolich, Jr. |
| 5,106,609 A | 4/1992 | Bolich, Jr. |
| 5,106,613 A | 4/1992 | Hartnett et al. |
| RE34,584 E | 4/1994 | Grote |
| 5,389,676 A | 2/1995 | Michaels |
| 5,431,913 A | 7/1995 | Phillips |
| 5,587,155 A | 12/1996 | Ochiai et al. |
| 5,624,666 A | 4/1997 | Coffindaffer |
| 5,639,450 A | 6/1997 | Oldenhove de Guertechin |
| 5,674,478 A | 10/1997 | Dodd |
| 5,690,947 A | 11/1997 | Habif |
| 5,710,114 A | 1/1998 | Pyles |
| 5,750,122 A | 5/1998 | Evans |
| 5,776,872 A | 7/1998 | Giret et al. |
| 5,879,584 A | 3/1999 | Bianchetti et al. |
| 5,888,492 A | 3/1999 | Starch |
| 6,013,682 A | 1/2000 | Dalle |
| 6,117,915 A | 9/2000 | Pereira |
| 6,221,370 B1 | 4/2001 | Wadle et al. |
| 6,303,109 B1 | 10/2001 | Foerster et al. |
| 6,342,208 B1 | 1/2002 | Hyldgaard et al. |
| 6,407,051 B1 | 6/2002 | Smith et al. |
| 6,419,909 B1 | 7/2002 | Lorant et al. |
| 6,420,013 B1 | 7/2002 | Vinson et al. |
| 6,492,315 B1 | 12/2002 | Cao et al. |
| 6,528,070 B1 | 3/2003 | Bratescu et al. |
| 6,534,069 B1 | 3/2003 | Asmus et al. |
| 6,569,414 B1 | 5/2003 | Bernecker et al. |
| 6,602,494 B1 | 8/2003 | Jahedshoar et al. |
| 6,607,733 B1 | 8/2003 | Diec et al. |
| 6,616,917 B2 | 9/2003 | Lorant et al. |
| 6,649,155 B1 | 11/2003 | Dunlop |
| 6,878,773 B2 | 4/2005 | Marteaux et al. |
| 7,268,107 B2 | 9/2007 | Nieendick et al. |
| 7,297,717 B2 | 11/2007 | Iwai et al. |
| 7,476,393 B2 | 1/2009 | Dubief et al. |
| 7,588,797 B2 | 9/2009 | Skoog et al. |
| 7,647,630 B2 | 1/2010 | Arroyo et al. |
| 7,687,066 B2 | 3/2010 | Fujino et al. |
| 7,736,662 B2 | 6/2010 | Amari et al. |
| 7,833,516 B2 | 11/2010 | Fack et al. |
| 7,833,517 B2 | 11/2010 | Fack et al. |
| 7,871,601 B2 | 1/2011 | Watanabe |
| 7,887,857 B1 | 2/2011 | Johnson |
| 7,901,699 B2 | 3/2011 | Takase et al. |
| 7,975,295 B2 | 7/2011 | Arroyo et al. |
| 8,343,470 B2 | 1/2013 | Hloucha et al. |
| 8,372,382 B2 | 2/2013 | Norman |
| 8,454,941 B2 | 6/2013 | Ohrmann et al. |
| 8,501,823 B2 | 8/2013 | Fujino et al. |
| 8,501,973 B2 | 8/2013 | Schrodi et al. |
| 8,518,386 B2 | 8/2013 | Dierker et al. |
| 8,536,356 B2 | 9/2013 | Carvin et al. |
| 8,603,508 B2 | 12/2013 | Norman |
| 8,628,760 B2 | 1/2014 | Carter et al. |
| 8,642,824 B2 | 2/2014 | Lemke et al. |
| 8,658,581 B2 | 2/2014 | Hloucha et al. |
| 8,692,006 B2 | 4/2014 | Uptain et al. |
| 8,715,629 B2 | 5/2014 | Schmid et al. |
| 8,715,631 B2 | 5/2014 | Araujo et al. |
| 8,722,069 B2 | 5/2014 | Amalric et al. |
| 8,748,646 B2 | 6/2014 | Kluesener et al. |
| 8,765,651 B2 | 7/2014 | Hutton, III et al. |
| 8,815,257 B2 | 8/2014 | Braksmayer et al. |
| 8,815,264 B2 | 8/2014 | Wolff et al. |
| 8,821,844 B2 | 9/2014 | Dierker et al. |
| 8,865,193 B2 | 10/2014 | Wolff et al. |
| 8,883,698 B2 | 11/2014 | Scheibel et al. |
| 8,920,786 B2 | 12/2014 | Hloucha et al. |
| 8,933,131 B2 | 1/2015 | Federle et al. |
| 8,936,796 B2 | 1/2015 | Kitko et al. |
| 8,936,798 B2 | 1/2015 | Kitko et al. |
| 8,957,268 B2 | 2/2015 | Cohen et al. |
| 8,961,943 B2 | 2/2015 | Schroder et al. |
| 2001/0053374 A1 | 12/2001 | Darlrymple et al. |
| 2002/0051797 A1 | 5/2002 | Jezior |
| 2002/0168327 A1 | 11/2002 | Bailey |
| 2003/0083212 A1 | 5/2003 | Willard |
| 2003/0095990 A1 | 5/2003 | Hua et al. |
| 2003/0134771 A1 | 7/2003 | Ellson et al. |
| 2004/0048996 A1 | 3/2004 | Lange |
| 2004/0138400 A1 | 7/2004 | Lange |
| 2004/0234491 A1 | 11/2004 | Brautigam et al. |
| 2004/0258647 A1 | 12/2004 | Ruppert et al. |
| 2005/0031568 A1 | 2/2005 | Deckner |
| 2005/0031653 A1 | 2/2005 | Kwetkat et al. |
| 2005/0031659 A1 | 2/2005 | Deckner |
| 2005/0031660 A1 | 2/2005 | Deckner |
| 2005/0032916 A1 | 2/2005 | Deckner |
| 2005/0053634 A1 | 3/2005 | Ruppert et al. |
| 2005/0112157 A1 | 5/2005 | Ruppert et al. |
| 2005/0186167 A1 | 8/2005 | Ueda |
| 2006/0008482 A1 | 1/2006 | Prinz et al. |
| 2006/0013787 A1 | 1/2006 | Sebillotte-Arnaud |
| 2006/0018863 A1 | 1/2006 | Mougin et al. |
| 2006/0024256 A1 | 2/2006 | Wells et al. |
| 2006/0078525 A1 | 4/2006 | Tomokuni |
| 2006/0078528 A1 | 4/2006 | Yang |
| 2006/0096041 A1 | 5/2006 | Molenda |
| 2006/0099167 A1 | 5/2006 | Staudigel |
| 2006/0127344 A1 | 6/2006 | Zofchak |
| 2006/0165739 A1 | 7/2006 | Komesvarakul et al. |
| 2006/0286052 A1 | 12/2006 | Oki et al. |
| 2007/0041929 A1 | 2/2007 | Torgerson |
| 2007/0110696 A1 | 5/2007 | Johnson et al. |
| 2007/0128147 A1 | 6/2007 | Schwartz |
| 2007/0237798 A1 | 10/2007 | Apostol |
| 2007/0248562 A1 | 10/2007 | Berry |
| 2007/0275866 A1 | 11/2007 | Dykstra |
| 2007/0286837 A1 | 12/2007 | Torgerson |
| 2007/0298004 A1 | 12/2007 | Li |
| 2008/0057016 A1 | 3/2008 | Geary et al. |
| 2008/0206355 A1 | 8/2008 | Schwartz |
| 2008/0292574 A1 | 11/2008 | Uehara |
| 2008/0292575 A1 | 11/2008 | Uehara |
| 2008/0317698 A1 | 12/2008 | Wells |
| 2009/0041704 A1 | 2/2009 | Molenda et al. |
| 2009/0107062 A1 | 4/2009 | Pedersen |
| 2009/0130220 A1 | 5/2009 | Johnson |
| 2009/0143267 A1 | 6/2009 | Zhang |
| 2009/0220443 A1 | 9/2009 | Braksmayer |
| 2009/0232873 A1 | 9/2009 | Glenn, Jr. |
| 2009/0246236 A1* | 10/2009 | Kitko et al. .............. 424/401 |
| 2009/0258085 A1 | 10/2009 | Bach |
| 2009/0324527 A1 | 12/2009 | Okada et al. |
| 2009/0324528 A1 | 12/2009 | Okada et al. |
| 2009/0324529 A1 | 12/2009 | Okada et al. |
| 2009/0324531 A1 | 12/2009 | Okada et al. |
| 2009/0324532 A1 | 12/2009 | Okada et al. |
| 2010/0047499 A1 | 2/2010 | Braksmayer et al. |
| 2010/0143282 A1 | 6/2010 | Yokogi |

(56) References Cited

U.S. PATENT DOCUMENTS

| | | |
|---|---|---|
| 2010/0145086 A1 | 6/2010 | Schrodi et al. |
| 2010/0179083 A1 | 7/2010 | Glenn, Jr. |
| 2010/0215596 A1 | 8/2010 | Amela Conesa et al. |
| 2010/0316684 A1 | 12/2010 | Daniels |
| 2011/0020253 A1 | 1/2011 | Doyle |
| 2011/0028424 A1 | 2/2011 | Zhang et al. |
| 2011/0045039 A1 | 2/2011 | Sunkel |
| 2011/0070173 A1 | 3/2011 | Yoshida et al. |
| 2011/0113679 A1 | 5/2011 | Cohen et al. |
| 2011/0135587 A1 | 6/2011 | Kinoshita et al. |
| 2011/0160472 A1 | 6/2011 | Lemke et al. |
| 2011/0166370 A1 | 7/2011 | Saunders et al. |
| 2011/0311655 A1 | 12/2011 | Ross |
| 2012/0010303 A1 | 1/2012 | Mujkic et al. |
| 2012/0020909 A1 | 1/2012 | Courel et al. |
| 2012/0171263 A1 | 7/2012 | Capelas Romeu et al. |
| 2013/0280174 A1 | 10/2013 | Lipic et al. |
| 2013/0280192 A1* | 10/2013 | Carter et al. .......... 424/62 |
| 2013/0280193 A1 | 10/2013 | Carter et al. |
| 2013/0280356 A1 | 10/2013 | Stella et al. |
| 2013/0281551 A1 | 10/2013 | Stella et al. |
| 2013/0344012 A1 | 12/2013 | Cohen et al. |
| 2014/0219936 A1 | 8/2014 | Amalric et al. |
| 2014/0275595 A1 | 9/2014 | Wampler et al. |
| 2014/0275681 A1 | 9/2014 | Cohen et al. |
| 2014/0302103 A1 | 10/2014 | Carter |
| 2014/0309154 A1 | 10/2014 | Carter |
| 2014/0357714 A1 | 12/2014 | Braksmayer et al. |
| 2014/0377205 A1 | 12/2014 | Uehara et al. |
| 2015/0059995 A1 | 3/2015 | Ramaratnam et al. |
| 2015/0360015 A1 | 12/2015 | Rabe et al. |
| 2015/0360016 A1 | 12/2015 | Rabe et al. |
| 2016/0067153 A1 | 3/2016 | Chen et al. |
| 2016/0090555 A1 | 3/2016 | Frankenbach et al. |
| 2016/0095807 A1 | 4/2016 | Stella et al. |
| 2016/0095808 A1 | 4/2016 | Okada et al. |
| 2016/0095809 A1 | 4/2016 | Stella et al. |
| 2016/0244698 A1 | 8/2016 | Schubert et al. |
| 2016/0244915 A1 | 8/2016 | Mohammadi et al. |

FOREIGN PATENT DOCUMENTS

| | | |
|---|---|---|
| CN | 101032451 A | 9/2007 |
| CN | 101664369 A | 3/2010 |
| CN | 102389378 A | 3/2012 |
| DE | 2130485 A1 | 12/1972 |
| DE | 19732015 C1 | 7/1998 |
| DE | 19710155 A1 | 9/1998 |
| DE | 19851451 A1 | 5/2000 |
| DE | 19903717 A1 | 8/2000 |
| DE | 19907408 A1 | 8/2000 |
| DE | 19943585 A1 | 3/2001 |
| DE | 10237735 A1 | 2/2004 |
| DE | 10239647 A1 | 3/2004 |
| DE | 10239712 A1 | 3/2004 |
| DE | 102004025287 A1 | 12/2005 |
| DE | 102004062771 A1 | 6/2006 |
| DE | 102007028027 A1 | 12/2008 |
| DE | 102011088928 A1 | 8/2012 |
| DE | 102011015192 A1 | 9/2012 |
| EP | 60372 A1 | 9/1982 |
| EP | 437956 A1 | 7/1991 |
| EP | 482417 A1 | 4/1992 |
| EP | 0472184 B1 | 10/1994 |
| EP | 716848 A1 | 6/1996 |
| EP | 739619 A1 | 10/1996 |
| EP | 1055707 A1 | 11/2000 |
| EP | 1815841 A1 | 8/2007 |
| EP | 2243462 A1 | 10/2010 |
| EP | 2505180 A1 | 10/2012 |
| FR | 2853544 A1 | 10/2004 |
| FR | 2863873 A1 | 6/2005 |
| FR | 2930436 A1 | 10/2009 |
| FR | 2930442 A1 | 10/2009 |
| FR | 2967084 A1 | 5/2012 |
| GB | 849433 A | 9/1992 |
| GB | 2455294 A | 6/2009 |
| GB | 2485834 A | 5/2012 |
| JP | 55147214 A | 11/1980 |
| JP | 59160532 A | 9/1984 |
| JP | 3284611 A | 4/1994 |
| JP | 6262060 A | 9/1994 |
| JP | 8089786 A | 4/1996 |
| JP | 8259990 A | 10/1996 |
| JP | 9143027 A | 6/1997 |
| JP | 9301835 A | 11/1997 |
| JP | H107532 | 1/1998 |
| JP | 10036221 A1 | 2/1998 |
| JP | 10139632 A1 | 5/1998 |
| JP | 10180085 A1 | 7/1998 |
| JP | 11043416 A1 | 2/1999 |
| JP | 11090211 A1 | 4/1999 |
| JP | 2000128735 A | 5/2000 |
| JP | 2000189785 A | 7/2000 |
| JP | 2001011486 A | 1/2001 |
| JP | 2001048744 A | 2/2001 |
| JP | 2001072532 A | 3/2001 |
| JP | 2002-053893 A | 2/2002 |
| JP | 2002193740 A | 7/2002 |
| JP | 2002212029 A | 7/2002 |
| JP | 2002338440 A | 11/2002 |
| JP | 2002338499 A | 11/2002 |
| JP | 2003040732 A | 2/2003 |
| JP | 2003055128 A | 2/2003 |
| JP | 2003327506 A | 11/2003 |
| JP | 2004067649 A | 3/2004 |
| JP | 2004238354 A | 8/2004 |
| JP | 2004269502 A | 9/2004 |
| JP | 2004307414 A | 11/2004 |
| JP | 2004359587 A | 12/2004 |
| JP | 4069320 A | 1/2005 |
| JP | 2005075817 A | 3/2005 |
| JP | 2005132794 A | 5/2005 |
| JP | 2005132806 A | 5/2005 |
| JP | 2005187465 A | 7/2005 |
| JP | 2005239674 A | 9/2005 |
| JP | 2005306872 A | 11/2005 |
| JP | 2005350409 A | 12/2005 |
| JP | 2006160619 A | 6/2006 |
| JP | 2006169198 A | 6/2006 |
| JP | 2006273752 A | 10/2006 |
| JP | 2006298890 A | 11/2006 |
| JP | 2007153754 A | 6/2007 |
| JP | 2007169240 A | 7/2007 |
| JP | 2007223938 A | 9/2007 |
| JP | 2007254404 A | 10/2007 |
| JP | 2007254405 A | 10/2007 |
| JP | 2007269722 A | 10/2007 |
| JP | 2007269740 A | 10/2007 |
| JP | 2007277181 A | 10/2007 |
| JP | 2008105952 A | 5/2008 |
| JP | 2008255044 A | 10/2008 |
| JP | 2008297280 A | 12/2008 |
| JP | 2009084238 A | 4/2009 |
| JP | 2009114081 A | 5/2009 |
| JP | 2009126791 A | 6/2009 |
| JP | 2009126843 A | 6/2009 |
| JP | 2009137850 A | 6/2009 |
| JP | 2009137914 A | 6/2009 |
| JP | 2009137915 A | 6/2009 |
| JP | 2009149554 A | 7/2009 |
| JP | 2009161520 A | 7/2009 |
| JP | 2009242269 A | 10/2009 |
| JP | 2009275017 A | 11/2009 |
| JP | 2009292732 A | 12/2009 |
| JP | 2010043027 A | 2/2010 |
| JP | 2010053150 A | 3/2010 |
| JP | 2010195739 A | 9/2010 |
| JP | 2010222317 A | 10/2010 |
| JP | 2010235567 A | 10/2010 |
| JP | 2010248178 A | 11/2010 |
| JP | 2010280643 A | 12/2010 |
| JP | 2010280644 A | 12/2010 |
| JP | 2011001289 A | 1/2011 |

(56) References Cited

FOREIGN PATENT DOCUMENTS

| | | |
|---|---|---|
| JP | 2011073976 A | 4/2011 |
| JP | 2011088882 A | 5/2011 |
| JP | 2011126796 A | 6/2011 |
| JP | 2011126797 A | 6/2011 |
| JP | 2011132143 A | 7/2011 |
| JP | 2011144133 A | 7/2011 |
| JP | 2011173843 A | 9/2011 |
| JP | 2011178667 A | 9/2011 |
| JP | 2011190222 A | 9/2011 |
| JP | 2011213681 A | 10/2011 |
| JP | 2011213682 A | 10/2011 |
| JP | 2011246400 A | 12/2011 |
| JP | 2012001597 A | 1/2012 |
| JP | 2012036119 A | 2/2012 |
| JP | 2012077000 A | 4/2012 |
| JP | 2012077001 A | 4/2012 |
| JP | 2012082150 A | 4/2012 |
| JP | 2012082151 A | 4/2012 |
| JP | 2012111723 A | 6/2012 |
| JP | 2012116783 A | 6/2012 |
| JP | 2012131762 A | 7/2012 |
| JP | 2012144466 A | 8/2012 |
| JP | 2012201683 A | 10/2012 |
| JP | 2012206971 A | 10/2012 |
| JP | 2012207000 A | 10/2012 |
| JP | 2012207001 A | 10/2012 |
| KR | 2001036921 A | 5/2001 |
| KR | 2002043422 A | 6/2002 |
| KR | 2008074315 A | 8/2008 |
| KR | 2009073368 A | 7/2009 |
| KR | 2011101411 A | 9/2011 |
| RU | 2020921 C1 | 10/1994 |
| RU | 2025118 C1 | 12/1994 |
| RU | 2026668 C1 | 1/1995 |
| WO | 9112880 A1 | 9/1991 |
| WO | 9406410 A1 | 3/1994 |
| WO | 9505145 A1 | 2/1995 |
| WO | 9614046 A1 | 5/1996 |
| WO | 9723192 A1 | 7/1997 |
| WO | WO99/24003 A1 | 5/1999 |
| WO | 0037166 A | 6/2000 |
| WO | 0040213 A | 7/2000 |
| WO | 0064408 A | 11/2000 |
| WO | 0100143 A | 1/2001 |
| WO | 0101934 A | 1/2001 |
| WO | 0106993 A | 2/2001 |
| WO | 03020237 A | 3/2003 |
| WO | 03051319 A | 6/2003 |
| WO | 2007051527 A1 | 5/2007 |
| WO | WO 2007/103398 A1 | 9/2007 |
| WO | WO 2007/103398 A1 | 9/2007 |
| WO | 2008007059 A1 | 1/2008 |
| WO | WO2008/032284 A1 | 3/2008 |
| WO | 2008043470 A1 | 4/2008 |
| WO | WO 2008/091681 A2 | 7/2008 |
| WO | WO 2009/020665 A1 | 2/2009 |
| WO | WO 2009/020667 A1 | 2/2009 |
| WO | 2009115428 A1 | 9/2009 |
| WO | WO2009/107062 A2 | 9/2009 |
| WO | 2010143802 A1 | 12/2010 |
| WO | WO 2011/049932 A1 | 4/2011 |
| WO | 2011129784 A2 | 10/2011 |
| WO | WO 2011/120780 A2 | 10/2011 |
| WO | 2012002210 A1 | 1/2012 |
| WO | WO 2012/006324 A1 | 1/2012 |
| WO | WO 2012/009525 A2 | 1/2012 |
| WO | 2012130413 A2 | 10/2012 |
| WO | 2012130954 A1 | 10/2012 |
| WO | 2012131624 A1 | 10/2012 |

OTHER PUBLICATIONS

"Delivering Solutions, Creating Value", Jun. 25, 2009.
International Search Report; PCT/US2013/035428; Mailing Date Jun. 17, 2014.
International Search Report; PCT/US2013/035431; Mailing Date Jun. 17, 2014.
International Search Report; PCT/US2014/033018; Mailing Date May 30, 2014.
International Search Report; PCT/US2014/032907; Mailing Date Sep. 15, 2014.
Michael Starch: "New Cosmetic Ingredients Based on Soybean Oil", 1P.com Journal, 1P.com Inc., West Henrietta, NY, US, Jun. 15, 2007 (Jun. 15, 2007).
Morioka, H., "Effects of Zinc on the New Preparation Method of Hydroxy Double Salts" Inorg. Chem. 1999, 38, 4211-6.
PCT/US2013/035428; Mailing Date Oct. 30, 2014; 8 pages.
PCT/US2013/035431; Mailing Date Oct. 30, 2014; 8 pages.
Solarek, D. B., "Cationic Starches in Modified Starches: Properties and Uses", Wurzburg, O. B., Ed., CRC Press, Inc., Boca Raton, Fla. 1986, pp. 113-125.
U.S. Appl. No. 14/995,431, filed Jan. 14, 2016, Callens et al.
U.S. Appl. No. 14/995,446, filed Jan. 14, 2016, Callens et al.
U.S. Appl. No. 14/873,654, filed Oct. 2, 2015, Stella et al.
U.S. Appl. No. 14/506,209, filed Oct. 3, 2014, Stella et al.
U.S. Appl. No. 14/506,229, filed Oct. 3, 2014, Stella et al.
PCT International Search Report and Written Opinion for PCT/US2015/053608 dated Dec. 1, 2015.
PCT International Search Report and Written Opinion for PCT/US2015/053451 dated Dec. 16, 2015.
PCT International Search Report and Written Opinion for PCT/US2016/018372; dated Jun. 7, 2016.
PCT International Search Report and Written Opinion for PCT/US2016/018376 dated May 2, 2016.
All Office Actions U.S. Appl. No. 15/044,312 (P&G Case 13712).
Schrock, Richard R., et al.; Molybdenum and Tungsten Imido Alkylidene Complexes as Efficient Olefin-Metathesis Catalysts; Angewandte Chemie Int. Ed.; 2003; pp. 4592-4633; vol. 42.
Schrock, Richard R.; High Oxidation State Multiple Metal-Carbon Bonds; Chemical Reviews; 2002; pp. 145-179; vol. 102; No. 1.
Schrock, Richard R.; Recent Advances in High Oxidation State Mo and W Imido Alkylidene Chemistry; Chemical Reviews; 2009; pp. 3211-3226; vol. 109; No. 8.
PCT International Search Report and Written Opinion for PCT/US2015/053609 dated Dec. 7, 2015.
Encyclopedia of Polymer Science and Engineering, vol. 15, 2d ed., pp. 204-308, "Silicones" John Wiley & Sons, Inc. (1989).
"DPG-Industrial", Data Sheet, Shell Chemicals, Issued Oct. 23, 2009.
"Benzyl alcohol" from Wikipedia, last modified Feb. 2, 2016, printed Mar. 15, 2016.
"Tallow Amines", Chemicalland21.com, printed Mar. 16, 2016.
"Myristic acid", from Wikipedia, last modified Dec. 3, 2015, printed Mar. 15, 2016.
PCT International Search Report and Written Opinion for PCT/US2016/013571 dated Apr. 1, 2016.
Hydetaka Akatsuka et al., "Effect of polyols on the shear-induced structure and rheological properties of behenyl trimethyl ammonium chloride/1-octadecanol/water ternary systems", Colloids and Surfaces A: Physiochem. Eng. Aspects 326 (2008) 169-174.
PCT International Search Report and Written Opinion for PCT/US2016/013573 dated Apr. 19, 2016.

* cited by examiner

PERSONAL CARE COMPOSITION COMPRISING A PRE-EMULSIFIED FORMULATION

FIELD OF THE INVENTION

The present invention relates to a personal care composition containing a pre-emulsified emulsion selected from the group comprising metathesized unsaturated polyol esters, sucrose polyesters, fatty esters and mixtures thereof, an anionic surfactant, an aqueous carrier, wherein the composition is stable with respect to emulsion particle size, viscosity and visual phase separation, and methods of using the same.

BACKGROUND OF THE INVENTION

Human hair and skin become soiled due to its contact with the surrounding environment and from the sebum secreted by the scalp. The soiling of hair and skin causes it to have a dirty feel and an unattractive appearance.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils.

A variety of approaches have been developed to alleviate these after-shampoo problems. One approach is the application of hair shampoos which attempt to both cleanse and condition the hair from a single product.

In order to provide hair conditioning benefits in a cleansing shampoo base, a wide variety of conditioning actives have been proposed. However, including active levels of conditioning agents in shampoos may result in rheology and stability issues, creating consumer trade-offs in cleaning, lather profiles, and weigh-down effects. Additionally, the rising costs of silicone and the petroleum based nature of silicone have minimized silicone's desirability as a conditioning active.

Based on the foregoing, there is a need for a conditioning active which can provide conditioning benefits to hair and skin and can replace, or be used in combination with silicone, or other conditioning actives, to maximize the conditioning activity of hair care compositions. Additionally, there is a desire to find a conditioning active which can be derived from a natural source, thereby providing a conditioning active derived from a renewable resource. Numerous conditioning actives derived from a natural source have been used in hair and skin care compositions. However, due to the hydrophobic nature of these actives, their strong interactions with the micellar surfactant system cause product instability, such as viscosity reduction and phase separation. Consequentially, it is generally difficult to formulate meaningful levels of hydrocarbon based natural conditioning actives to provide significant benefits from rinse off applications. There is a desire to enhance the formulation flexibility and the deposition of these conditioner actives to provide consumer noticeable benefits.

Therefore, there is also a desire to find a conditioning active that is both derived from a natural source and leads to a stable product comprising a micellar surfactant system.

SUMMARY OF THE INVENTION

The present invention is directed to the combination of the use of conditioning actives selected from the group comprising metathesized unsaturated polyol esters, sucrose polyesters, fatty esters having a molecular weight of 1500 or higher and the pre-emulsions of such conditioning actives with particle size of from about 20 nanometers to 20 microns, in an embodiment from about 0.1-5 µm to significantly improve the stability, deposition and hair conditioning benefits of hair care compositions. The present invention is directed to a personal care composition comprising from about 0.25% to about 80% of a pre-emulsified emulsion comprising from about 0.005% to about 80% of one or more materials selected from the group comprising metathesized unsaturated polyol esters, sucrose polyesters, fatty esters having a molecular weight of 1500 or higher and mixtures thereof or, by weight of said hair care composition; wherein an emulsifier is selected from the group consisting of anionic, non-ionic, cationic, amphoteric and mixtures thereof and further wherein the average particle size of the pre-emulsified emulsion is from about 20 nanometers to 20 microns, in a further embodiment may be from about 100 nm to 1 micron; from about 5% to about 50% of one or more anionic surfactants, by weight of said hair care composition; at least about 20% of an aqueous carrier, by weight of said hair care composition wherein the composition is stable with respect to emulsion particle size, viscosity and visual phase separation.

These and other features, aspects, and advantages of the present invention will become evident to those skilled in the art from a reading of the present disclosure.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The terms "include," "includes," and "including," as used herein, are meant to be non-limiting and are understood to mean "comprise," "comprises," and "comprising," respectively.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated. The term "weight percent" may be denoted as "wt. %" herein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

A. Emulsion

The term "pre-emulsion" in this patent application describes any stable emulsion or dispersion of a conditioning material (or other material?) such as oil, viscous liquid, viscoelastic liquid, or solid in an aqueous medium, separately prepared and used as one of the components of a personal care composition.

The same pre-emulsion can be used as a component of different personal care products provided that it is compatible with the other components of the personal care products.

Stable means that the viscosity, particle size, and other important characteristics of the emulsion do not significantly change over reasonable time under exposure to typical temperature, moisture, pressure, shear, light and other environmental conditions that the pre-emulsion is exposed during packing, storage, and transportation.

Historically, naturals and natural derivatives are used primarily as image ingredients in personal care applications due to their instability in chasses especially high surfactant systems. The use of active emulsions presents 3 advantages in the present invention: i) Additional emulsifiers in the emulsion reduce the interactions of actives with the surfactants in the chassis, which in turn enhances product stability; ii) Emulsified actives, especially those with higher viscosities, potentially improve spreadibility on hair surfaces with different properties (e.g. virgin vs. damaged hair); iii) Emulsions significantly affect the appearance of a clear chassis. Emulsions with a particle size in the range of 100-500 nm alters clear to translucent appearance, which consumers perceive as more benefit ingredients in the product.

1 Conditioning actives:

a. Metathesized Oligomer

The hair care composition may comprise from about 0.05% to about 15%, alternatively from about 0.1% to about 10%, and alternatively from about 0.25% to about 5%, of one or more oligomers derived from metathesis of unsaturated polyol esters, by weight of said hair care composition. Exemplary metathesized unsaturated polyol esters and their starting materials are set forth in U.S. Patent Application U.S. 2009/0220443 A1, which is incorporated herein by reference.

A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis). Self-metathesis may be represented schematically as shown in Equation I:

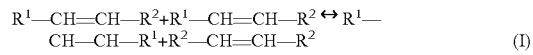

(I)

where $R^1$ and $R^2$ are organic groups.

Cross-metathesis may be represented schematically as shown in Equation II:

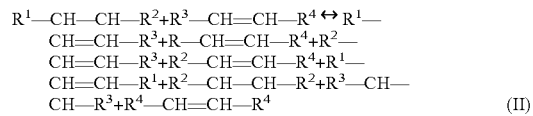

(II)

where $R^1$, $R^2$, $R^3$, and $R^4$ are organic groups.

When the unsaturated polyol ester comprises molecules that have more than one carbon-carbon double bond (i.e., a polyunsaturated polyol ester), self-metathesis results in oligomerization of the unsaturated polyol ester. The self-metathesis reaction results in the formation of metathesis dimers, metathesis trimers, and metathesis tetramers. Higher order metathesis oligomers, such as metathesis pentamers and metathesis hexamers, may also be formed by continued self-metathesis and will depend on the number and type of chains connecting the unsaturated polyol ester material as well as the number of esters and orientation of the ester relative to the unsaturation As a starting material, metathesized unsaturated polyol esters are prepared from one or more unsaturated polyol esters. As used herein, the term "unsaturated polyol ester" refers to a compound having two or more hydroxyl groups wherein at least one of the hydroxyl groups is in the form of an ester and wherein the ester has an organic group including at least one carbon-carbon double bond. In many embodiments, the unsaturated polyol ester can be represented by the general structure I:

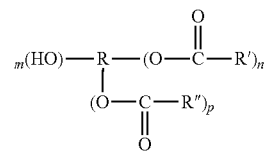

where n≥1; m≥0; p≥0; (n+m+p)≥2; R is an organic group; R is an organic group having at least one carbon-carbon double bond; and R" is a saturated organic group. Exemplary embodiments of the unsaturated polyol ester are described in detail in U.S. 2009/0220443 A1.

In many embodiments of the invention, the unsaturated polyol ester is an unsaturated ester of glycerol. Sources of unsaturated polyol esters of glycerol include synthesized oils, natural oils (e.g., vegetable oils, algae oils, bacterial derived oils, and animal fats), combinations of theses, and the like. Recycled used vegetable oils may also be used. Representative examples of vegetable oils include argan oil, canola oil, rapeseed oil, coconut oil, corn oil, cottonseed oil, olive oil, palm oil, peanut oil, safflower oil, sesame oil, soy-bean oil, sunflower oil, high oleoyl soy-bean oil, high oleoyl sunflower oil, linseed oil, palm kernel oil, tung oil, castor oil, high erucic rape oils, Jatropha oil, combinations of theses, and the like. Representative examples of animal fats include lard, tallow, chicken fat, yellow grease, fish oil, combinations of these, and the like. A representative example of a synthesized oil includes tall oil, which is a byproduct of wood pulp manufacture.

Other examples of unsaturated polyol esters include diesters such as those derived from ethylene glycol or propylene glycol, esters such as those derived from pentaerythritol or dipentaerythritol, or sugar esters such as SEFOSE®. Sugar esters such as SEFOSE® include one or more types of sucrose polyesters, with up to eight ester groups that could undergo a metathesis exchange reaction. Sucrose polyesters are derived from a natural resource and therefore, the use of sucrose polyesters can result in a positive environmental impact. Sucrose polyesters are polyester materials, having multiple substitution positions around the sucrose backbone coupled with the chain length, saturation, and derivation variables of the fatty chains. Such sucrose polyesters can have an esterification ("IBAR") of greater than about 5. In one embodiment the sucrose polyester may have an IBAR of from about 5 to about 8. In another embodiment the sucrose polyester has an IBAR of about 5-7, and in another embodiment the sucrose polyester has an IBAR of about 6. In yet another embodiment the sucrose polyester has an IBAR of about 8. As sucrose polyesters are derived from a natural resource, a distribution in the IBAR and chain length may exist. For example a sucrose polyester having an IBAR of 6, may contain a mixture of mostly IBAR of about 6, with some IBAR of about 5 and some IBAR of about 7. Additionally, such sucrose polyesters may have a saturation or iodine value ("IV") of about 3 to about 140. In another embodiment the sucrose polyester may have an IV of about 10 to about 120. In yet another embodiment the sucrose polyester may have an IV of about 20 to 100. Further, such sucrose polyesters have a chain length of about $C_{12}$ to $C_{20}$ but are not limited to these chain lengths.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio.

Other examples of suitable natural polyol esters may include but not be limited to sorbitol esters, maltitol esters, sorbitan esters, maltodextrin derived esters, xylitol esters, and other sugar derived esters.

In other embodiments, chain lengths of esters are not restricted to C8-C22 or even chain lengths only and can include natural esters that come from co-metathesis of fats and oils with short chain olefins both natural and synthetic providing a polyol ester feedstock which can have even and odd chains as well as shorter and longer chains for the self metathesis reaction. Suitable short chain olefins include ethylene and butene.

The oligomers derived from the metathesis of unsaturated polyol esters may be further modified via hydrogenation. For example, in certain embodiments, the oligomer can be about 60% hydrogenated or more; in certain embodiments, about 70% hydrogenated or more; in certain embodiments, about 80% hydrogenated or more; in certain embodiments, about 85% hydrogenated or more; in certain embodiments, about 90% hydrogenated or more; and in certain embodiments, generally 100% hydrogenated.

In some embodiments, the triglyceride oligomer is derived from the self-metathesis of soybean oil. The soy oligomer can include hydrogenated soy polyglycerides. The soy oligomer may also include $C_{15}$-$C_{23}$ alkanes, as a byproduct. An example of metathesis derived soy oligomers is the fully hydrogenated DOW CORNING® HY-3050 soy wax, available from Dow Corning.

In other embodiments, the metathesized unsaturated polyol esters can be used as a blend with one or more non-metathesized unsaturated polyol esters. The non-metathesized unsaturated polyol esters can be fully or partially hydrogenated. Such an example is DOW CORNING® HY-3051, a blend of HY-3050 oligomer and hydrogenated soybean oil (HSBO), available from Dow Corning. In some embodiments of the invention, the non-metathesized unsaturated polyol ester is an unsaturated ester of glycerol. Sources of unsaturated polyol esters of glycerol include synthesized oils, natural oils (e.g., vegetable oils, algae oils, bacterial derived oils, and animal fats), combinations of theses, and the like. Recycled used vegetable oils may also be used. Representative examples of vegetable oils include those listed above.

Other modifications of the polyol ester oligomers can be partial amidation of some fraction of the esters with ammonia or higher organic amines such as dodecyl amine or other fatty amines. This modification will alter the overall oligomer composition but can be useful in some applications providing increased lubricity of the product. Another modification can be via partial amidation of a poly amine providing potential for some pseudo cationic nature to the polyol ester oligomers. Such an example is DOW CORNING® material HY-3200. Other exemplary embodiments of amido functionalized oligomers are described in detail in WO2012006324A1, which is incorporated herein by reference.

The polyol ester oligomers may also be modified further by partial hydroformylation of the unsaturated functionality to provide one or more OH groups and an increase in the oligomer hydrophilicity.

a. Non-Metathesized Sugar Polyesters

The personal care composition may also comprise from about 0.05% to about 15%, alternatively from about 0.1% to about 10%, and alternatively from about 0.25% to about 5%, of one or more of sugar polyesters, by weight of said personal care composition. Typical examples of sucrose polyesters such as SEFOSE®. The sucrose molecule can be esterified in one or more of its eight hydroxyl groups with saturated or unsaturated carboxylic acids, providing a very diverse set of possible molecular structures of polyesters. The possibility of metathesis of these species was described in page 7 of this document. However, the non-metathesized unsaturated sucrose polyesters or saturated sucrose polyesters and their mixtures can also be used as conditioning material in hair care and body wash compositions.

b. Mixtures of Conditioning Materials

The personal care composition may also comprise of one or more materials selected from the group of metathesized oligomers, sucrose polyesters, other fatty esters, or other conditioning materials (silicone or non-silicone 2 Emulsifiers Emulsifiers are selected for each conditioning active is guided by the Hydrophilic-Lipophilic-Balance value (HLB value) of emulsifiers. Suitable range of HLB value is 6-16, more preferably 8-14. Emulsifiers with a HLB higher than 10 are water soluble. Emulsifiers with low HLB are lipid soluble. To obtain suitable HLB value, a mixture of two or more emulsifiers may be used. Suitable emulsifiers include non-ionic, cationic, anionic and amphoteric emulsifiers.

The concentration of the emulsifier in the emulsion should be sufficient to provide desired the emulsification of the conditioning active to achieve desired particle size and emulsion stability, and generally ranges from about 0.1 wt %-about 50 wt %, from about 1 wt %-about 30 wt %, from about 2 wt %-about 20 wt %, for example.

Non-ionic emulsifiers suitable for use in the emulsion may include a wide variety of emulsifiers are useful herein and include, but not limited to, those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN(Registered trademark) 80), sorbitan sesquioleate (e.g., Arlacel(Registered trademark) 83), sorbitan monoisostearate (e.g., CRILL(Registered trademark) 6 made by Croda), sorbitan stearates (e.g., SPAN (Registered trademark) 60), sorbitan triooleate (e.g., SPAN (Registered trademark) 85), sorbitan tristearate (e.g., SPAN (Registered trademark) 65), sorbitan dipalmitates (e.g., SPAN(Registered trademark) 40), and sorbitan isostearate. Sorbitan monoisostearate and sorbitan sesquioleate are particularly preferred emulsifiers for use in the present invention.

Other suitable emulsifiers for use in the present invention include, but is not limited to, glyceryl monoesters, preferably glyceryl monoesters of C16-C22 saturated, unsaturated and branched chain fatty acids such as glyceryl oleate, glyceryl monostearate, glyceryl monopalmitate, glyceryl monobehenate, and mixtures thereof; polyglyceryl esters of C16-C22 saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of C16-C22 saturated, unsaturated and branched chain fatty acids such as methyl glucose dioleate, methyl glucose sesquiisostearate, and mixtures thereof; sucrose fatty acid esters, preferably sucrose esters of C12-C22 saturated, unsaturated and branched chain fatty acids such as sucrose stearate, sucrose trilaurate, sucrose distearate (e.g., Crodesta(Registered trademark) F10), and mixtures thereof; C12-C22 ethoxylated fatty alcohols such as oleth-2, oleth-3, steareth-2, and mixtures thereof; hydrogenated castor oil ethoxylates such as PEG-7 hydrogenated castor oil; sorbitan ester ethoxylates such as PEG-40 sorbitan peroleate, Polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof.

In addition to these primary emulsifiers, the compositions of the present invention can optionally contain a coemulsifier to provide additional water-lipid emulsion stability. Suitable coemulsifiers include, but is not limited to, phosphatidyl cholines and phosphatidyl choline-containing compositions such as lecithins; long chain C16-C22 fatty acid salts such as sodium stearate; long chain C16-C22 dialiphatic, short chain C1-C4 dialiphatic quaternary ammonium salts such as ditallow dimethyl ammonium chloride and ditallow dimethyl ammonium methylsulfate; long chain C16-C22 dialkoyl(alkenoyl)-2-hydroxyethyl, short chain C1-C4 dialiphatic quaternary ammonium salts such as ditallowoyl-2-hydroxyethyl dimethyl ammonium chloride; the long chain C16-C22 dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain C1-C4 dialiphatic, long chain C16-C22 monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries).

Anionic emulsifiers suitable for use in the emulsion of the present invention. A variety of anionic emulsifiers can be used in the personal care composition as described herein. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

In addition, anionic emulsifiers that have acrylate functionality may also be used in the instant shampoo compositions. Anionic emulsifiers useful herein include, but aren't limited to: poly(meth)acrylic acid; copolymers of (meth) acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; Polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

Cationic Emulsifers suitable for use in the emulsion of the present invention may include a wide variety of emulsifiers are useful herein and include, but not limited to: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt The cationic emulsifier is included in the composition at a level by weight of from about 0.1% to about 10%, preferably from about 0.5% to about 8%, more preferably from about 0.8% to about 5%, still more preferably from about 1.0% to about 4%.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

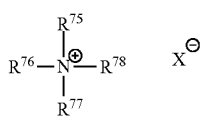

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

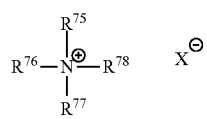

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

Amphoteric emulsifiers suitable for use in the emulsion may include a wide variety of emulsifiers useful herein and include, but not limited to those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include cocoamphoacetate, cocoamphodiacetate, lauroamphoacetate, lauroamphodiacetate, and mixtures thereof.

C. Aqueous Carrier

The hair care compositions can be in the form of pourable liquids (under ambient conditions). Such compositions will therefore typically comprise a carrier, which is present at a level of from about 20 wt % to about 95 wt %, or even from about 60 wt % to about 85 wt %. The carrier may comprise water, or a miscible mixture of water and organic solvent, and in one aspect may comprise water with minimal or no significant concentrations of organic solvent, except as otherwise incidentally incorporated into the composition as minor ingredients of other components.

The carrier useful in embodiments of the hair care composition includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol. Nonlimiting examples of water-miscible solvents include those selected from the group consisting of alcohols having from about 1 to about 6 carbon atoms, polyols having from about 1 to about 10 carbon atoms, ketones having from about 3 to about 4 carbon atoms, C1-C6 esters of C1-C6 alcohols, sulfoxides, amides, carbonate esters, ethoxylated and propoxylated C1-C10 alcohols, lactones, pyrollidones, and mixtures thereof. Preferred water-miscible solvents are those selected from the group consisting of ethanol, 2-propanol, propylene glycol, buylene glycol, and mixtures thereof.

3 Additional Components a. Preservative:

Non-limiting examples of preservatives which may be used in the leave-on composition of the present invention are benzyl alcohol, methyl paraben, propyl paraben, DMDM hydanoin, methylchloroisothiaoline, methylisothiazolinone, and imidazolidinyl urea.

b. pH Adjustment.

The pH of the emulsions may be important to the stability of the emulsion and their interaction with a personal care composition. For example, naturally occurring methylated phenols in natural oils may incur oxidation to cause emulsion color alteration at higher pH. In an embodiment of the present invention, pH is less than about pH 7, but higher than 3.5. Typical bases and acids can be used to adjust pH. Non-limiting examples include, sodium hydroxide aqueous solution and citric acid.

4 Method of Making Pre-Emulsion

Making the emulsion comprising components below is to pre-emulsify the conditioning active before their addition to the hair care composition. A non-limiting example of a method of making is provided below. All oil soluble components are mixed in a vessel. Heat may be applied to allow mixture to liquidify. All water soluble components are mixed in a separate vessel and heated to about same temperature as the oil phase. The oil phase and aqueous phase are mixed under a high shear mixer (example, Turrax mixer by IKA). The particle size of the conditioning active is in the range of 0.01-5 μm, in a further embodiment is in the range of 0.05-1 μm, and in yet a further embodiment is in the range of 0.1-0.5 μm. High energy mixing device may be needed to achieve desired particle size. High energy mixing device include, but not limited to Microfluidizer from Microfluidics Corp., Sonolator from Sonic Corp., Colloid mill from Sonic Corp.

5. Stability

The stability of a personal care composition can be measured by composition viscosity/rheology, particle size and visual observations of phase separation over a period of time. Detailed methods are described in "Method" section. The length of time can be measured by days, weeks and months. Typical measuring temperatures are room temperature, e.g. about 25° C., and/or at elevated temperature, e.g. 40° C.

6. Composition Appearance

Without the addition of other opacifying agents, surfactant systems often appear clear. With the addition of the pre-emulsions, the composition appearance may vary from, translucent to opaque. The opacity of the composition depends on the particle size of the active in the pre-emulsion, the amount of the pre-emulsion added and the optical path length. A simple way to differentiate translucent from opaque appearance is to dispense a small amount of composition into the center of the palm of a hand. Translucent compositions allow naked eye to observe the skin color underneath the product without being complete transparent. A naked eye cannot see palm skin color through the composition. The ability to adjust the composition appearance with the pre-emulsions provides the flexibility to modify composition appearance to consumer liking.

In other embodiments, the unsaturated polyol esters and blends can be modified prior to oligomerization to incorporate near terminal branching. Exemplary polyol esters modified prior to oligomerization to incorporate terminal branching are set forth in WO2012/009525 A2, which is incorporated herein by reference.

B. Surfactant

The hair care composition may comprise a detersive surfactant, which provides cleaning performance to the composition. The detersive surfactant in turn comprises an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the hair care composition should be sufficient to provide the desired cleaning and lather performance, and generally ranges from about 2 wt % to about 50 wt %, from about 5 wt % to about 30 wt %, from about 8 wt % to about 25 wt %, or from about 10 wt % to about 20 wt %. Accordingly, the hair care composition may comprise a detersive surfactant in an amount of about 5 wt %, about 10 wt %, about 12 wt %, about 15 wt %, about 17 wt %, about 18 wt %, or about 20 wt %, for example.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the hair care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the hair care composition herein include those which are known for use in hair care or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include cocoamphoacetate, cocoamphodiacetate, lauroamphoacetate, lauroamphodiacetate, and mixtures thereof.

Zwitterionic detersive surfactants suitable for use in the hair care composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety. Structured Surfactants—The composition of the present invention, when in a multiphase form, may comprise structured surfactant that is suitable for application to keratinous tissue such as skin and/or hair. The part of the composition which contains the structured surfactant can comprise in one embodiment at least about 50% of anisotropic phase, and in a different embodiment from about 50% to about 90% of an anisotropic phase. Structured surfactants may comprise anionic, nonionic, cationic, zwitterionic, amphoteric surfactants, soap, and combinations thereof, as disclosed herein and in US 2007/0248562 A1, in combination with a suitable structurant. The choice of a suitable combination of a surfactant and structurant is within the knowledge of one of skill in the art. Alkylamphoacetates are suitable structured surfactants used in the multiphase compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isostearyth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The structured surfactant may be in the form of a discrete structured domain, visibly distinct from the non-structured domain. Where the composition comprises both a structured and a non-structured phase, the structured domain can enable the incorporation of high levels of skin care actives that are not otherwise emulsified in the composition. In a particular embodiment the structured domain is an opaque structured domain. The opaque structured domain may be a lamellar phase, and may be a lamellar phase that produces a lamellar gel network. In one embodiment, the structured surfactant is in the form of a lamellar phase, which provides resistance to shear, adequate yield to suspend particles and droplets, desirable rheology characteristics, and/or long term stability. The lamellar phase tends to have a viscosity that minimizes the need for viscosity modifiers.

Non-limiting examples of suitable structurants are described in U.S. Pat. No. 5,952,286, and include unsaturated and/or branched long chain (C8-C24) liquid fatty acids or ester derivative thereof, unsaturated and/or branched long chain liquid alcohol or ether derivatives thereof, and mixtures thereof. The structured surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25 deg. C.

The composition can comprise both an anisotropic and/or an isotropic phase. In a particular embodiment, the structured surfactant is in a visibly distinct phase of the composition.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof. An electrolyte, if used, can be added per se to the multiphase composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate. The electrolyte may be added to the structured surfactant phase of the multiphase composition in the amount of from about 0.1 wt % to about 15 wt % by weight, preferably from about 1 wt % to about 6 wt % by weight, more preferably from about 3 wt % to about 6 wt %, by weight of the structured surfactant composition. In one embodiment of the present invention, the personal care composition comprises a structured surfactant phase comprising a mixture of at least one nonionic surfactant, and an electrolyte. In another embodiment, the surfactant phase can comprise a mixture of surfactants, water, at least one anionic surfactant, an electrolyte, and at least one alkanolamide.

In an embodiment, the composition comprises an anionic surfactant and a non-ionic co-surfactant. In another embodiment the surfactant system is free, or substantially free of sulfate materials. Suitable sulfate free surfactants are disclosed in WO publication 2011/120780 and WO publication 2011/049932.

D. Additional Components

The hair care composition may further comprise one or more additional components known for use in hair care or personal care products, provided that the additional components do not otherwise unduly impair product stability, aesthetics, or performance. Such optional ingredients are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the personal care compositions.

Non-limiting examples of additional components for use in the hair care composition include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

In one embodiment, the hair care compositions comprise one or more conditioning agents. Conditioning agents include materials that are used to give a particular conditioning benefit to hair and/or skin. The conditioning agents useful in the hair care compositions typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

One or more conditioning agents are present from about 0.01 wt % to about 10 wt %, alternatively from about 0.1 wt % to about 8 wt %, and alternatively from about 0.2 wt % to about 4 wt %, by weight of the composition.

a. Silicones

The conditioning agent of the hair care composition may be an insoluble silicone conditioning agent. The silicone conditioning agent particles may comprise volatile silicone, non-volatile silicone, or combinations thereof. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, by weight of the composition, alternatively from about 0.1% to about 8%, alternatively from about 0.1% to about 5%, and alternatively from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the hair care composition may have a viscosity, as measured at 25Â° C., from about 20 to about 2,000,000 centistokes ("csk"), alternatively from about 1,000 to about 1,800,000 csk, alternatively from about 50,000 to about 1,500,000 csk, and alternatively from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, alternatively from about 0.01 micrometer to about 2 micrometer, and alternatively from about 0.01 micrometer to about 0.5 micrometer. For larger particle application to hair, the volume average particle diameters typically range from about 5 micrometer to about 125 micrometer, alternatively from about 10 micrometer to about 90 micrometer, alternatively from about 15 micrometer to about 70 micrometer, and alternatively from about 20 micrometer to about 50 micrometer.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

i. Silicone Oils

Silicone fluids include silicone oils, which are flowable silicone materials having a viscosity, as measured at 25° C., less than 1,000,000 csk, alternatively from about 5 csk to about 1,000,000 csk, and alternatively from about 100 csk to about 600,000 csk. Suitable silicone oils for use in the hair care composition include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (I):

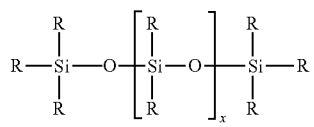

wherein R is aliphatic, in some embodiments alkyl, alkenyl, or aryl, R can be substituted or unsubstituted, and x is an integer from 1 to about 8,000. Suitable R groups for use in the compositions include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Possible alkyl and alkenyl substituents include $C_1$ to $C_5$ alkyls and alkenyls, alternatively from $C_1$ to $C_4$, and alternatively from C to $C_2$. The aliphatic portions of other alkyl-, alkenyl-, or alkynyl-containing groups (such as alkoxy, alkaryl, and alkamino) can be straight or branched chains, and may be from $C_1$ to $C_5$, alternatively from $C_1$ to $C_4$, alternatively from $C_1$ to $C_3$, and alternatively from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length may be as described herein.

ii. Amino and Cationic Silicones

Cationic silicone fluids suitable for use in the compositions include, but are not limited to, those which conform to the general formula (II):

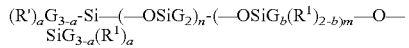

wherein G is hydrogen, phenyl, hydroxy, or $C_1$-$C_8$ alkyl, in some embodiments, methyl; a is 0 or an integer having a value from 1 to 3; b is 0 or 1; n is a number from 0 to 1,999, alternatively from 49 to 499; m is an integer from 1 to 2,000, alternatively from 1 to 10; the sum of n and m is a number from 1 to 2,000, alternatively from 50 to 500; $R^1$ is a monovalent radical conforming to the general formula $CqH_{2q}L$, wherein q is an integer having a value from 2 to 8 and L is selected from the following groups:

—$N(R^2)CH_2$—$CH_2$—$N(R^2)_2$
—$N(R^2)_2$
—$N(R^2)_3A^-$
—$N(R^2)CH_2$—$CH_2$—$NR^2H_2A^-$ wherein $R^2$ is hydrogen, phenyl, benzyl, or a saturated hydrocarbon radical, in some embodiments an alkyl radical from about $C_1$ to about $C_{20}$, and $A^-$ is a halide ion.

In one embodiment, the cationic silicone corresponding to formula (II) is the polymer known as "trimethylsilylamodimethicone", which is shown below in formula (III):

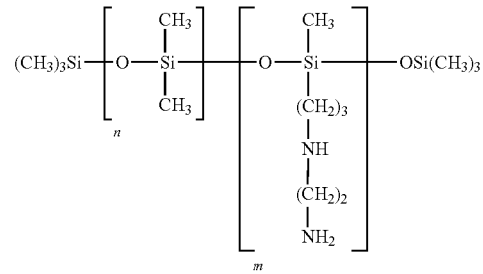

Other silicone cationic polymers which may be used in the hair care composition are represented by the general formula (IV):

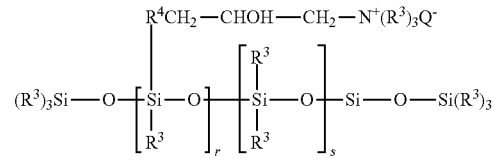

wherein $R^3$ is a monovalent hydrocarbon radical from $C_1$ to $C_{18}$, in some embodiments an alkyl or alkenyl radical, such as methyl; $R_4$ is a hydrocarbon radical, in some embodiments a $C_1$ to $C_{18}$ alkylene radical or a $C_{10}$ to $C_{18}$ alkyleneoxy radical, alternatively a $C_1$ to $C_8$ alkyleneoxy radical; $Q^-$ is a halide ion, in some embodiments chloride; r is an average statistical value from 2 to 20, in some embodiments from 2 to 8; s is an average statistical value from 20 to 200, in some embodiments from 20 to 50. One polymer of this class is known as UCARE SILICONE ALE 56®, available from Union Carbide.

iii. Silicone Gums

Other silicone fluids suitable for use in the hair care composition are the insoluble silicone gums. These gums are polyorganosiloxane materials having a viscosity, as measured at 25° C., of greater than or equal to 1,000,000 csk.

Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76, all of which are incorporated herein by reference. Specific non-limiting examples of silicone gums for use in the hair care include polydimethylsiloxane, (polydimethylsiloxane)(methylvinylsiloxane)copolymer, poly(dimethylsiloxane)(diphenyl siloxane)(methylvinylsiloxane)copolymer and mixtures thereof.

iv. High Refractive Index Silicones

Other non-volatile, insoluble silicone fluid conditioning agents that are suitable for use in the hair care composition are those known as "high refractive index silicones," having a refractive index of at least about 1.46, alternatively at least about 1.48, alternatively at least about 1.52, and alternatively at least about 1.55. The refractive index of the polysiloxane fluid will generally be less than about 1.70, typically less than about 1.60. In this context, polysiloxane "fluid" includes oils as well as gums. The high refractive index polysiloxane fluid includes those represented by general Formula (I) above, as well as cyclic polysiloxanes such as those represented by Formula (V) below:

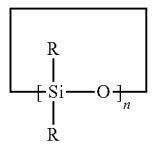

wherein R is as defined above, and n is a number from about 3 to about 7, alternatively from about 3 to about 5.

The high refractive index polysiloxane fluids contain an amount of aryl-containing R substituents sufficient to increase the refractive index to the desired level, which is described herein. Additionally, R and n may be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, alternatively at least about 20%, alternatively at least about 25%, alternatively at least about 35%, and alternatively at least about 50%. Typically, the degree of aryl substitution will be less than about 90%, more generally less than about 85%, alternatively from about 55% to about 80%. In some embodiments, the high refractive index polysiloxane fluids have a combination of phenyl or phenyl derivative substituents, with alkyl substituents, in some embodiments $C_1$-$C_4$ alkyl, hydroxy, or $C_1$-$C_4$ alkylamino (especially-$R^4NHR^5NH2$ wherein each $R^4$ and $R^5$ independently is a $C_1$-$C_3$ alkyl, alkenyl, and/or alkoxy).

When high refractive index silicones are used in the hair care composition, they may be used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the hair care composition are disclosed in U.S. Pat. No. 2,826,551, U.S. Pat. No. 3,964,500, U.S. Pat. No. 4,364,837, British Pat. No. 849,433, and Silicon Compounds, Petrarch Systems, Inc. (1984), all of which are incorporated herein by reference.

v. Silicone Resins

Silicone resins may be included in the silicone conditioning agent of the hair care composition. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Silicone resins for use in the hair care composition may include, but are not limited to MQ, MT, MTQ, MDT and MDTQ resins. Methyl is a possible silicone substituent. In some embodiments, silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, may be from about 4:1 to about 400:1, alternatively from about 9:1 to about 200:1, and alternatively from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

b. Organic Conditioning Oils

The conditioning agent of the hair care hair care composition may also comprise at least one organic conditioning oil, either alone or in combination with other conditioning agents, such as the silicones described above.

i. Hydrocarbon Oils

Suitable organic conditioning oils for use as conditioning agents in the hair care composition include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils may be from about $C_{12}$ to about $C_{19}$. Branched chain hydrocarbon oils, including hydrocarbon polymers, typically will contain more than 19 carbon atoms.

ii. Polyolefins

Organic conditioning oils for use in the hair care composition can also include liquid polyolefins, alternatively liquid poly-α-olefins, alternatively hydrogenated liquid poly-α-olefins. Polyolefins for use herein are prepared by polymerization of $C_4$ to about $C_{14}$ olefinic monomers, in some embodiments from about $C_6$ to about $C_{12}$.

iii. Fatty Esters

Other suitable organic conditioning oils for use as the conditioning agent in the hair care hair care composition include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.). The fatty esters may be unsaturated, partially hydrogenated or fully hydrogenated.

iv. Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones.

v. Fatty Alcohols

Other suitable organic conditioning oils for use in the personal care hair care composition include, but are not limited to, fatty alcohols having at least about 10 carbon atoms, alternatively from about 10 to about 22 carbon atoms, and alternatively from about 12 to about 16 carbon atoms.

vi. Alkyl Glucosides and Alkyl Glucoside Derivatives

Suitable organic conditioning oils for use in the personal care hair care composition include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

c. Other Conditioning Agents i. Quaternary Ammonium Compounds

Suitable quaternary ammonium compounds for use as conditioning agents in the personal care hair care composition include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

ii. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

iii. Cationic Deposition Polymers

The personal care composition may further comprise a cationic deposition polymer. Any known natural or synthetic cationic deposition polymer can be used herein. Examples include those polymers disclosed in U.S. Pat. No. 6,649,155; U.S. Patent Application Publication Nos. 2008/0317698; 2008/0206355; and 2006/0099167, which are incorporated herein by reference in their entirety.

The cationic deposition polymer is included in the composition at a level from about 0.01 wt % to about 1 wt %, in one embodiment from about 0.05 wt % to about 0.75 wt %, in another embodiment from about 0.25 wt % to about 0.50 wt %, in view of providing the benefits of the hair care composition.

The cationic deposition polymer is a water soluble polymer with a charge density from about 0.5 milliequivalents per gram to about 12 milliequivalents per gram. The cationic deposition polymer used in the composition has a molecular weight of about 100,000 Daltons to about 5,000,000 Daltons. The cationic deposition polymer is a low, medium or high charge density cationic polymer.

These cationic deposition polymers can include at least one of (a) a cationic guar polymer, (b) a cationic non-guar polymer, (c) a cationic tapioca polymer, (d) a cationic copolymer of acrylamide monomers and cationic monomers, and/or (e) a synthetic, non-crosslinked, cationic polymer, which forms lyotropic liquid crystals upon combination with the detersive surfactant. Additionally, the cationic deposition polymer can be a mixture of deposition polymers.

(1) Cationic Guar Polymers

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol. from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.6%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Another guar hydroxypropyltrimonium chloride with a charge density of about 1.1 meq/g and a M.Wt. of about 500,000 g/mole is available from Ashland. A further guar hydroxypropyltrimonium chloride with a charge density of about 1.5 meq/g and a M.Wt. of about 500,000 g/mole is available from Ashland.

Other suitable polymers include: Hi-Care 1000, which has a charge density of about 0.7 meq/g and a M.Wt. of about 600,000 g/mole and is available from Rhodia; N-Hance 3269 and N-Hance 3270, which have a charge density of about 0.7 meq/g and a M.Wt. of about 425,000 g/mole and is available from Ashland; AquaCat CG518 has a charge density of about 0.9 meq/g and a M.Wt. of about 50,000 g/mole and is available from Ashland. A further non-limiting example is N-Hance 3196 from Ashland.

(2) Cationic Non-Guar Polymers

The shampoo compositions of the present invention comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

The galactomannan polymer derivatives for use in the shampoo compositions of the present invention have a molecular weight from about 1,000 to about 10,000,000. In one embodiment of the present invention, the galactomannan polymer derivatives have a molecular weight from about 5,000 to about 3,000,000. As used herein, the term "molecular weight" refers to the weight average molecular weight. The weight average molecular weight may be measured by gel permeation chromatography.

The shampoo compositions of the present invention include galactomannan polymer derivatives which have a cationic charge density from about 0.9 meq/g to about 7 meq/g. In one embodiment of the present invention, the galactomannan polymer derivatives have a cationinc charge density from about 1 meq/g to about 5 meq/g. The degree of substitution of the cationic groups onto the galactomannan structure should be sufficient to provide the requisite cationic charge density.

(3) Cationically Modified Starch Polymer

The shampoo compositions of the present invention comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions of the present invention comprise cationically modified starch polymers at a range of about 0.01% to about 10%, and more preferably from about 0.05% to about 5%, by weight of the composition.

Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof. Tapioca starch is preferred.

In one embodiment of the present invention, cationically modified starch polymers are selected from degraded cationic maize starch, cationic tapioca, cationic potato starch, and mixtures thereof. In another embodiment, cationically modified starch polymers are cationic corn starch and cationic tapioca. Cationic tapioca starch is preferred.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starch, guar, cellulose, *cassia*, locust bean, konjac, tara, galactomannan, and tapioca. In a further embodiment, cationic deposition polymers are selected from Mirapol® 100S (Rhodia), Jaguar® C17, polyqueaternium-6, cationic tapioca starch (Akzo), polyquaternium-76, and mixtures thereof.

(4) Cationic Copolymer of an Acrylamide Monomer and a Cationic Monomer

According to an embodiment of the present invention, the shampoo composition comprises a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

(5) Cationic Synthetic Polymer

The cationic polymer described herein aids in providing damaged hair, particularly chemically treated hair, with a surrogate hydrophobic F-layer. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al.

The concentration of the cationic polymers ranges about 0.025% to about 5%, preferably from about 0.1% to about 3%, more preferably from about 0.2% to about 1%, by weight of the shampoo composition.

The cationic polymers have a cationic charge density of from about 2 meq/gm to about 7 meq/gm, preferably from about 3 meq/gm to about 7 meq/gm, more preferably from about 4 meq/gm to about 7 meq/gm. In some embodiments, the cationic charge density is about 6.2 meq/gm. The polymers also have a molecular weight of from about 1,000 to about 5,000,000, more preferably from about 10,000 to about 2,000,000, most preferably 100,000 to about 2,000,000. where X—=halogen, hydroxide, alkoxide, sulfate or alkylsulfate.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Preferred cationic monomers comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Preferred cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

More preferred cationic monomers include trimethyl ammonium propyl (meth)acrylamido chloride.

In an embodiment of the present invention, thickening agents and suspending agents, such as xanthan gum, guar gum, starch and starch derivatives, viscosity modifiers such as methanolamides of long chain fatty acids, cocomonoethanol amide, salts such as sodium potassium chloride and sulfate and crystalline suspending agents, and pearlescent aids such as ethylene glycol distearate may be used.

In an embodiment of the present invention, the viscosity-modifying substance is a thickening polymer, chosen from copolymers of at least one first monomer type, which is chosen from acrylic acid and methacrylic acid, and at least one second monomer type, which is chosen from esters of acrylic acid and ethoxylated fatty alcohol; crosslinked polyacrylic acid; crosslinked copolymers of at least one first monomer type, which is chosen from acrylic acid and methacrylic acid, and at least one second monomer type, which is chosen from esters of acrylic acid with C10- to C30-alcohols; copolymers of at least one first monomer type, which is chosen from acrylic acid and methacrylic acid, and at least one second monomer type, which is chosen from esters of itaconic acid and ethoxylated fatty alcohol; copolymers of at least one first monomer type, which is chosen from acrylic acid and methacrylic acid, at least one second monomer type, which is chosen from esters of itaconic acid and ethoxylated C10- to C30-alcohol and a third monomer type, chosen from C1- to C4-aminoalkyl acrylates; copolymers of two or more monomers chosen from acrylic acid, methacrylic acid, acrylic esters and methacrylic esters; copolymers of vinylpyrrolidone and ammonium acryloyldimethyltaurate; copolymers of ammonium acryloyldimethyltaurate and monomers chosen from esters of methacrylic acid and ethoxylated fatty alcohols; hydroxyethylcellulose; hydroxypropylcellulose; hydroxypropylguar; glyceryl polyacrylate; glyceryl polymethacrylate; copolymers of at least one C2-, C3- or C4-alkylene and styrene; polyurethanes; hydroxypropyl starch phosphate; polyacrylamide; copolymer of maleic anhydride and methyl vinyl ether crosslinked with decadiene; carob seed flour; guar gum; xanthan; dehydroxanthan; carrageenan; karaya gum; hydrolyzed corn starch; copolymers of polyethylene oxide, fatty alcohols and saturated methylenediphenyl diisocyanate (e.g. PEG-150/stearyl alcohol/SMDI copolymer).

e. Benefit Agents

In an embodiment, the personal care composition further comprises one or more additional benefit agents. The benefit agents comprise a material selected from the group consisting of anti-dandruff agents, vitamins, lipid soluble vitamins, chelants, perfumes, brighteners, enzymes, sensates, attractants, anti-bacterial agents, dyes, pigments, bleaches, and mixtures thereof.

In one aspect said benefit agent may comprise an anti-dandruff agent. Such anti-dandruff particulate should be physically and chemically compatible with the components of the composition, and should not otherwise unduly impair product stability, aesthetics or performance.

According to an embodiment, the personal care composition comprises an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt.

Pyridinethione particulates are suitable particulate antidandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the personal care composition, the azole anti-microbial active is included in an amount of from about 0.01 wt % to about 5 wt %, or from about 0.1 wt % to about 3 wt %, or from about 0.3 wt % to about 2 wt %. In an embodiment, the azole anti-microbial active is ketoconazole. In an embodiment, the sole anti-microbial active is ketoconazole.

Embodiments of the personal care composition may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001 wt % to about 10 wt %, or from about 0.01 wt % to about 7 wt %, or from about 0.1 wt % to about 5 wt % of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^+ A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x}+2x\,A^-\cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm$^2$. The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm$^2$, or at least about 2.5 microgram/cm$^2$, or at least about 3 microgram/cm$^2$, or at least about 4 microgram/cm$^2$, or at least about 6 microgram/cm$^2$, or at least about 7 microgram/cm$^2$, or at least about 8 microgram/cm$^2$, or at least about 8 microgram/cm$^2$, or at least about 10 microgram/cm$^2$. The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Embodiments of the personal care composition may also comprise fatty alcohol gel networks, which have been used for years in cosmetic creams and hair conditioners. These gel networks are formed by combining fatty alcohols and surfactants in the ratio of about 1:1 to about 40:1 (alternatively from about 2:1 to about 20:1, and alternatively from about 3:1 to about 10:1). The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

Thus according to an embodiment, the fatty alcohol is included in the fatty alcohol gel network at a level by weight of from about 0.05 wt % to about 14 wt %. For example, the fatty alcohol may be present in an amount ranging from about 1 wt % to about 10 wt %, and alternatively from about 6 wt % to about 8 wt %.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20, are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for the gel network composition.

TABLE 1

Gel network components

| Ingredient | Wt. % |
|---|---|
| Water | 78.27% |
| Cetyl Alcohol | 4.18% |
| Steary Alcohol | 7.52% |
| Sodium laureth-3 sulfate (28% Active) | 10.00% |
| 5-Chloro-2-methyl-4-isothiazolin-3-one, Kathon CG | 0.03% |

Test Methods

A. Emulsion Particle Size Method

This method is designed to measure the oil/lipid particle sizes in emulsion. It is an example of particle size measuring methodology. Other known particle size method may also be used. The Horiba LA-910 and LA-950 instruments use the principle of low-angle Fraunhofer diffraction and Light Scattering from the particles as the means to size particles in a dilution solution.

The emulsion sample is introduced into the horiba sampling cup, which contain a dilute dispersant solution. The sample is agitated in the sample cup and circulated through the flow cell. During the experiment, light from a laser and lamp are directed through the sample in the flow cell. The light from the laser and lamp diffracts and scatters off the particles and is detected by a seriew of detectors. The scattering and diffraction information travels from the detector to the computer, which then calculates the particle size distribution in the sample.

150 mL 1% sodium dodecyl sulfate (SDS) solution is added into a 400 mL beaker. About 0.5 (+/−) g of emulsion is weighed into the beaker. The sample is vigorously with a stir bar on a magnetic stirring plate for 5 minutes. The sample is ready for Particle Size Analysis by Horiba. Samples are analyzed within 10 minutes after sample preparation.

Horiba LA-910 Laser Scattering Particle Size Distribution Analyzer:

The appropriate measurement conditions are manually selected as listed below. The Horiba Cup is filled with 150 ml of 0.1% SDS using a measuring cylinder, then Sonicated, Circulated and Agitated through the cell. If the cell looks clean and background reading looks flat, a blank is run by pressing BLANK. The dispersed sample is added slowly with a disposable pipette to the Horiba cup while the dispersant solution is agitating and circulating through the Horiba system. Do not leave any sample in the syringe and the whole amount of the syringe is always added into the Horiba cup. The sample is added continuously and slowly until the % T of the Lamp is 90±2%. The sample is allowed to agitate and to circulate through the cell for 3 minutes, then press MEASURE to analyze the sample. Once the sample is analyzed, The cell is drained and cleaned with deionized water.

The Graph page is printed and the description of results is shown as D (50), also called the median, that is the particle size at which 50% of the particles are that size or smaller. D(20 and D(90) can also be generated if needed The particle size of oils and lipids in personal care composition is often difficult to measure with Particle Size Analyzers like Horiba L910. The particle sizes in the compositions are estimated via optical microscopy.

Hair Composition Stability Method Including Viscosity and Visual Assessment

The phase stability of the personal care composition is assessed with visual observations. The personal care composition appears homogeneous immediately after making. Two aliquots of about 50 mL of the composition are prepared in a plastic or glass jar covered with a lid. One jar is placed at room temperature, about 25° C., while the other is placed in a conventional oven at 40° C. Additional replicates may be prepared if desired. The samples at r.t. are observed approximately every week. The samples at 40° C. are observed after 1 week. Choices of other time durations are also acceptable. The samples at 40° C. are observed while warm and after cooled to room temperature. Samples with visible large particles, color alteration and/or two or more visible phases are considered instable.

The viscosity of the personal care composition is measured with Brookfield Viscometer RVDV-I Prime, or other conventional viscometer. The temperature of water bath is set to 25° C. Wingather Software and the CP41 spindle are selected. Following parameters are set, Mode: Timed Stop; Data Interval—00:01; # of Data Points-60; Speed—0.5 rpm. 2 g (2 mL) of a sample is placed in cup. The cup is then attached to the viscometer with arm clamp. The motor is then started and stopped after software collects 60 data points. The cup is then removed from the viscosmeter and cleaned with alcohol wipes. The viscosity of the composition is taken as the average of the readings after readings have reached a plateau or the last number. The viscosity dropped to below 7500 cP is considered instable. In an embodiment of the present invention, the viscosity of the composition 1 week at 40° C. should be about 4000 cPs or higher.

It is understood that the test methods that are disclosed in the Test Methods Section of the present application should be used to determine the respective values of the parameters of Applicants' invention as such invention is described and claimed herein.

B. Wet and Dry Conditioning Test Method

This test method is designed to allow for a subjective evaluation of the basic performance of conditioning shampoos for both wet combing and dry combing efficacy. The control treatments exemplified in Table 2 are (1) a clarifying shampoo that employs only surfactants and has no conditioning materials present, and (2) the same clarifying shampoo used in the washing process followed by the application of a mid-range hair conditioner. These treatments facilitate differentiation of performance of a set prototype conditioning shampoos. In a typical test, 3 to 5 separate formulations can be assessed for their performance. The substrate is virgin brown hair obtainable from a variety of sources that is screened to insure uniformity and lack of meaningful surface damage or low lift bleach damaged hair.

TABLE 2

| Clarifying Shampoo Formulation | | Silicone Containing Conditioner Formulation | |
| --- | --- | --- | --- |
| Ingredient | | Ingredient | Wt. % |
| Distilled Water | To 100% | Water | To 100% |
| Sodium Laureth-3 Sulfate | 7.00 | L-Glutamic Acid | 0.64 |
| Tetrasodium EDTA | 0.14 | Stearamidoproply-dimethylamine | 2.00 |
| Citric Acid (Anhy.) | 1.11 | Cetyl Alcohol | 2.50 |
| Sodium Citrate (dihydrate) | 0.00 | Stearyl Alcohol | 4.50 |
| Cocamide MEA | 0.50 | Dimethicone/Cyclomethicone (15/85 Blend) | 4.20 |
| Kathon CG | 0.03 | EDTA | 0.10 |
| Sodium Lauryl Sulfate | 7.00 | Benzyl Alcohol | 0.40 |
| DMDM Hydantoin | 0.10 | Kathon CG | 0.33 |
| Cocoamidopropyl Betaine | 2.00 | Perfume | 0.25 |
| NaCl | 0.70 | dl-Pantyl | 0.225 |
| Perfume | 0.46 | dl-Panthenol | 0.05 |

C. Treatment Procedure

Five 4 gram, 8 inch length switches are combined in a hair switch holder, wet for ten seconds with manipulation with 40° C. water of medium hardness (9-10 gpg) to ensure complete and even wetting. The switch is deliquored lightly and product is applied uniformly over the length of the combined switches from one inch below the holder towards the tip at a level of 0.1 gram product per one gram of dry hair (0.1 g/g of hair or 2 g for 20 g hair). For more concentrated prototypes the usage level is reduced to 0.05 g/g of hair. The switch combo is lathered for 30 seconds by a rubbing motion typical of that used by consumers and rinsed with 40° C. water flowing at 1.5 gal/min (with the hair being manipulated) for a further 30 seconds to ensure completeness. This step is repeated. For the control treatment with conditioner, it is applied in the same way as shampoo above, manipulated throughout the switch combo and rinsed thoroughly with manipulation, again for 30 seconds. The switches are deliquored lightly, separated from each other, hung on a rack so that they are not in contact and detangled with a wide tooth comb.

D. Grading Procedures

For wet combing evaluations using trained graders, the switches are separated on the rack into the five sets with one switch from each treatment included in the grading set. Only two combing evaluations are performed on each switch. The graders are asked to compare the treatments by combing with a narrow tooth nylon comb typical of those used by consumers and rate the ease/difficulty on a zero to ten scale. Ten separate evaluations are collected and the results analyzed by a statistical analysis package for establishing statistical significance. Control charting is regularly used to insure that the low and high controls separate into their regular domains. Statistical significance in differences between treatments is determined using Statgraphics Plus 5.1. All conditioning prototypes should be more than two LSDs above the clarifying control to be viewed as acceptable.

For dry combing evaluations, the switches from above are moved into a controlled temperature and humidity room (22° C./50% RH) and allowed to dry overnight. They remain separated as above and panelists are requested to evaluate dry conditioning performance by making three assessments; dry combing ease of the middle of the switch, dry combing ease of the tips, and a tactile assessment of tip feel. The same ten point scale is used for these comparisons. Again, only two panelists make an assessment of each switch set. Statistical analysis to separate differences is done using the same method as above.

E. Method

The hair contact angles are calculated using the Wilhelmy equation from the value of the wetting force of a single hair fiber as it inserted in water along its length.

EXAMPLES

The following examples illustrate the present invention. The exemplified compositions can be prepared by conventional formulation and mixing techniques. It will be appreciated that other modifications of the hair care composition within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following examples in Tables 3 and 4 are representative of hair care compositions encompassed by embodiments of the present invention.

TABLE 3

| Ingredient | Ex. 1 | Ex. 2 | Ex. 3 | Ex. 4 | Ex. 5 | Ex. 6 | Ex7 | Ex8 | Ex. 9 |
|---|---|---|---|---|---|---|---|---|---|
| Emulsion Examples | | | | | | | | | |
| Distilled Water | q.s. | q.s. | q.s. | q.s. | q.s. | q.s. | q.s. | q.s. | |
| Polysorbate[1] | 1.73 | 1.91 | 10 | 0.66 | — | — | 1.73 | 1.73 | — |
| Sorbitan Ester[2] | 0.77 | — | — | — | — | — | 0.77 | 0.77 | — |
| Sodium Laureth-3 Sulfate[3] | — | — | — | — | 5.0 | — | — | — | — |
| Monoglyceride[4] | — | 0.97 | — | 0.34 | — | — | — | — | — |
| Cocoamidopropyl Betaine[5] | — | — | — | — | — | 5.0 | — | — | — |
| Soy Oligomer[6] | — | 10.0 | — | — | — | — | — | — | — |
| Soy Oligomer Blend[7] | 20.0 | — | — | 20.0 | 20.0 | 20.0 | — | — | 20 |
| Sefose[8] | — | — | 20.0 | — | — | — | — | — | — |
| Glycerine[9] | — | 7.5 | 50.0 | 45.0 | — | — | — | — | 50 |
| Ethylene glycol[10] | 6.0 | — | — | — | — | — | 6.0 | 6.0 | — |
| Soybean oil[11] | — | — | — | — | — | — | 20.0 | — | — |
| Hydrogenated soybean oil[12] | — | — | — | — | — | — | — | 20.0 | — |
| $C_{12-14}$ pareth-9[13] | — | — | — | — | — | — | — | — | 2.1 |
| Stearamidopropyl dimethylamine[14] | — | — | — | — | — | — | — | — | 0.4 |
| Preservatives, pH, viscosity adjustment | Up to 3% | Up to 3% | Up to 3% | Up to 3% | Up to 3% | Up to 3% | Up to 3% | Up to 3% | Up to 3% |
| Median Particle Size, nm | 202 | 676 | 91 | 443 | 296 | 339 | 119 | 487 | 238 |

[1] Tween 20, from Lonza
[2] Span 60, from Croda
[3] Sodium Laureth 3 Sulphate (28% active), from P & G
[4] Glyceryle monooleate, from BASF
[5] Amphosol HCA-B, from Stepan
[6] HY-3050, from Dow Corning
[7] HY-3051, from Dow Corning
[8] Sefose 1618S from P & G
[9] Glycerin USP
[10] Ethylene glycol from Aldrich
[11] Soybean oil, from Cargill
[12] Soy-125, from Candlewic Co.
[13] BT9 from Nikkol
[14] Lexamine S-13 from Inolex Chemical Co

| | Comparative | | Present Invention | |
|---|---|---|---|---|
| Ingredient | Ex. 9 | Ex. 10 | Ex. 11 | Ex. 12 |
| Water | q.s. | q.s. | q.s. | q.s. |
| PQ-76[4] | 0.25 | 0.25 | 0.25 | 0.25 |
| Sodium Laureth Sulfate[5] | 6.0 | 6.0 | 6.0 | 6.0 |
| Sodium Lauryl Sulfate[6] | 5.5 | 5.5 | 5.5 | 5.5 |
| CMEA[7] | 0.85 | 0.85 | 0.85 | 0.85 |
| Cocoamidopropyl Betaine[8] | 2.0 | 2.0 | 2.0 | 2.0 |
| Soy Oligomer blend emulsion (ex. 1)[9] | — | — | 2.5 | — |
| Soy Oligomer Blend[10] | 0.5 | — | — | — |
| Sefose[11] | — | 0.5 | — | — |
| Sefose emulsion (ex. 3) | — | — | — | 2.5 |
| Fragrance | 0.65 | 0.65 | 0.65 | 0.65 |
| Preservatives, pH, viscosity adjustment | Up to 3% | Up to 3% | Up to 3% | Up to 3% |
| Particle size, μm | 2-15 | 3-5 | 0.2 | 0.09 |
| Visual phase stability, 1 week at 40° C. | Separation 2 phases | Separation 2 phases | No separation | No separation |

[1] C-500, from Rhodia
[2] Cationic Cassia, MW = 300,000; 4.25% Nitrogen, from Lubrizol Advanced Materials
[3] LR400, from Amerchol
[4] Mirapol AT-1 (10% active), from Rhodia
[5] Sodium Laureth Sulfate (28% active), from P&G
[6] Sodium Lauryl Sulfate (29% active), from P&G
[7] Ninol Comf, (85% active) from Stepan
[8] Amphosol HCA-B (30% active), from Stepan
[9] HY-3050, from Dow Corning
[10] HY-3051, from Dow Corning
[11] Sefose 1618S, from P&G

TABLE 6

Shampoo Compositions

| | Example compositions | | | | | | | | | | | | |
|---|---|---|---|---|---|---|---|---|---|---|---|---|---|
| | 13 | 14 | 15 | 16 | 17 | 18 | 19 | 20 | 21 | 22 | 23 | 24 | 25 |
| Sodium Laureth Sulfate ($SLE_3S$) (1) | | | | | | | | | | | | | |
| Sodium Laureth Sulfate ($SLE_1S$) (2) | 10.5 | 10.5 | 10.5 | 10.5 | 10.5 | 10.5 | 10.5 | 10.5 | 12 | 12 | 12 | 12 | 12 |
| Sodium Lauryl Sulfate (SLS) (4) | 1.5 | 1.5 | 1.5 | 1.5 | 1.5 | 1.5 | 1.5 | 1.5 | | | | | |
| Lauryl Hydroxysultaine (5) | 1 | 1 | 1 | 1 | 1 | 1 | 1 | 1 | | | | | |
| Cocamidopropyl Betaine (6) | | | | | | | | | 1.5 | 1.5 | 1.5 | 1.5 | 1.5 |
| HY-3050 Emulsion (7) | 5.0 | | | | | | | | | | | | |
| HY-3051 Emulsion (8) | | 2.5 | | | | | | | 2.5 | 2.5 | 2.5 | 2.5 | 2.5 |
| Sefose Emulsion (9) | | | 2.5 | | | | | | | | | | |
| Sefose Emulsion (10) | | | | 5.0 | | | | | | | | | |
| Soybean oil (11) | | | | | 2.5 | | | | | | | | |
| Hydrogenated soybean oil (12) | | | | | | 2.5 | | | | | | | |
| Soybean oil emulsion (13) | | | | | | | 2.5 | | | | | | |
| Hydrogenated soybean oil emulsion (14) | | | | | | | | 2.5 | | | | | |
| Cocamide MEA (15) | 1 | 1 | 1 | 1 | 1 | 1 | 1 | 1 | 1.5 | 1.5 | 1.5 | 1.5 | 1.5 |
| Glycol Distearate (16) | 1.5 | 1.5 | 1.5 | 1.5 | 1.5 | 1.5 | 1.5 | 1.5 | 1.5 | 1.5 | 1.5 | 1.5 | 1.5 |
| Zinc Pyrithione (17) | 1 | 1 | 1 | 1 | 1 | 1 | 1 | 1 | 1 | 1 | 1 | 1 | 1 |
| Zinc Carbonate (18) | 1.61 | 1.61 | 1.61 | 1.61 | 1.61 | 1.61 | 1.61 | 1.61 | 1.61 | 1.61 | 1.61 | 1.61 | 1.61 |
| Fragrance (19) | 0.7 | 0.7 | 0.7 | 0.7 | 0.7 | 0.7 | 0.7 | 0.7 | 0.7 | 0.7 | 0.7 | 0.7 | 0.7 |
| Guar Hyrdroxypropyltrimonium Chloride (LMW) (20) | | | | | | | | | | 0.3 | 0.3 | | |
| Polyquaternium-10 (HMW) (21) | | | | | | | | | | | 0.1 | 0.1 | |
| Poly (Dially) Dimethyl Ammonium Chloride (22) | | | | | | | | | | | | 0.2 | 0.2 |
| Guar Hyrdroxypropyltrimonium Chloride/ trimethylammoniopropyl-methacrylamide/acrylamide copolymer (23) | 0.6 | 0.6 | 0.6 | 0.6 | 0.6 | 0.6 | 0.6 | 0.6 | 0.6 | | | | |
| Stearyl Alcohol (24) | | | | | | | | | | | | 1.29 | 1.29 |
| Cetyl Alcohol (25) | | | | | | | | | | | | 0.71 | 0.71 |
| Hydrochloric acid (26) | QS | QS | QS | QS | QS | QS | QS | QS | QS | QS | QS | QS | QS |
| Preservative (27) | 0.05 | 0.05 | 0.05 | 0.05 | 0.05 | 0.05 | 0.05 | 0.05 | 0.05 | 0.05 | 0.05 | 0.05 | 0.05 |
| Sodium Chloride (28) | QS | QS | QS | QS | QS | QS | QS | QS | QS | QS | QS | QS | QS |
| Sodium Xylene Sulfonate (29) | QS | QS | QS | QS | QS | QS | QS | QS | QS | QS | QS | QS | QS |
| Sodium Benzoate (30) | 0.27 | 0.27 | 0.27 | 0.27 | 0.27 | 0.27 | 0.27 | 0.27 | 0.27 | 0.27 | 0.27 | 0.27 | 0.27 |
| Water and Minors (QS to 100%) (31) | QS | QS | QS | QS | QS | QS | QS | QS | QS | QS | QS | QS | QS |

| | Example compositions | | | | | | | | | | | | |
|---|---|---|---|---|---|---|---|---|---|---|---|---|---|
| | 26 | 27 | 28 | 29 | 30 | 31 | 32 | 33 | 34 | 35 | 36 | 37 | 38 |
| Sodium Laureth Sulfate ($SLE_3S$) (1) | | | | | | | | | | | | | |
| Sodium Laureth Sulfate ($SLE_1S$) (2) | 10.5 | 10.5 | 10.5 | 10.5 | 10.5 | 10.5 | 10.5 | 10.5 | 12 | 12 | 12 | 12 | 12 |
| Sodium Lauryl Sulfate (SLS) (4) | 1.5 | 1.5 | 1.5 | 1.5 | 1.5 | 1.5 | 1.5 | 1.5 | | | | | |
| Lauryl Hydroxysultaine (5) | 1 | 1 | 1 | 1 | 1 | 1 | 1 | 1 | | | | | |
| Cocamidopropyl Betaine (6) | | | | | | | | | 1.5 | 1.5 | 1.5 | 1.5 | 1.5 |
| HY-3050 Emulsion (7) | 5.0 | | | | | | | | | | | | |
| HY-3051 Emulsion (8) | | 2.5 | | | | | | | 2.5 | 2.5 | 2.5 | 2.5 | 2.5 |
| Sefose Emulsion (9) | | | 2.5 | | | | | | | | | | |
| Sefose Emulsion (10) | | | | 5.0 | | | | | | | | | |
| Soybean oil (11) | | | | | 2.5 | | | | | | | | |
| Hydrogenated soybean oil (12) | | | | | | 2.5 | | | | | | | |
| Soybean oil emulsion (13) | | | | | | | 2.5 | | | | | | |
| Hydrogenated soybean oil emulsion (14) | | | | | | | | 2.5 | | | | | |
| Cocamide MEA (15) | 1 | 1 | 1 | 1 | 1 | 1 | 1 | 1 | 1.5 | 1.5 | 1.5 | 1.5 | 1.5 |
| Glycol Distearate (16) | 1.5 | 1.5 | 1.5 | 1.5 | 1.5 | 1.5 | 1.5 | 1.5 | 1.5 | 1.5 | 1.5 | 1.5 | 1.5 |
| Zinc Pyrithione (17) | 1 | 1 | 1 | 1 | 1 | 1 | 1 | 1 | 1 | 1 | 1 | 1 | 1 |

TABLE 6-continued

| Shampoo Compositions | | | | | | | | | | | | | |
|---|---|---|---|---|---|---|---|---|---|---|---|---|---|
| Zinc Carbonate (18) | 1.61 | 1.61 | 1.61 | 1.61 | 1.61 | 1.61 | 1.61 | 1.61 | 1.61 | 1.61 | 1.61 | 1.61 | 1.61 |
| Fragrance (19) | 0.7 | 0.7 | 0.7 | 0.7 | 0.7 | 0.7 | 0.7 | 0.7 | 0.7 | 0.7 | 0.7 | 0.7 | 0.7 |
| Guar Hyrdroxypropyltrimonium Chloride (LMW) (20) | | | | | | | | | | 0.3 | 0.3 | | |
| Polyquaternium-10 (HMW) (21) | | | | | | | | | | 0.1 | 0.1 | | |
| Poly (Dially) Dimethyl Ammonium Chloride (22) | | | | | | | | | | | | 0.2 | 0.2 |
| Guar Hyrdroxypropyltrimonium Chloride/ trimethylammoniopropyl-methacrylamide/acrylamide copolymer (23) | 0.6 | 0.6 | 0.6 | 0.6 | 0.6 | 0.6 | 0.6 | 0.6 | 0.6 | | | | |
| Stearyl Alcohol (24) | | | | | | | | | | | 1.29 | | 1.29 |
| Cetyl Alcohol (25) | | | | | | | | | | | 0.71 | | 0.71 |
| Hydrochloric acid (26) | QS | QS | QS | QS | QS | QS | QS | QS | QS | QS | QS | QS | QS |
| Preservative (27) | 0.05 | 0.05 | 0.05 | 0.05 | 0.05 | 0.05 | 0.05 | 0.05 | 0.05 | 0.05 | 0.05 | 0.05 | 0.05 |
| Sodium Chloride (28) | QS | QS | QS | QS | QS | QS | QS | QS | QS | QS | QS | QS | QS |
| Sodium Xylene Sulfonate (29) | QS | QS | QS | QS | QS | QS | QS | QS | QS | QS | QS | QS | QS |
| Sodium Benzoate (30) | 0.27 | 0.27 | 0.27 | 0.27 | 0.27 | 0.27 | 0.27 | 0.27 | 0.27 | 0.27 | 0.27 | 0.27 | 0.27 |
| Water and Minors (QS to 100%) (31) | QS | QS | QS | QS | QS | QS | QS | QS | QS | QS | QS | QS | QS |

KEY:
(1). Sodium Laureth-3 Sulfate from the Stepan Company
(2). Sodium Laureth-1 Sulfate from the Stepan Company
(3). Glycerin from Procter & Gamble
(4). Sodium Lauryl Sulfate from Stepan Company
(5). Mackam LHS from Rhodia
(6). Amphosol HCA from Stepan Company
(7). HY-3050, from Dow Corning - Table 3, Example 2.emusion
(8). HY-3051, from Dow Corning - Table 3 - Example 1 emulsion
(9). Sefose - Table 3 Example 3 1618S, from P&G
(10). Sefose - Table Example 3 1618S, from P&G
(11). Soy Bean Oil from Cargil
(12). Soy125 soy wax from Candlewic Co
(13). Soybean oil emulsion - Table 3 Example 7
(14). Hydrogenated soybean oil emulsion - Table 3 Example 8
(15). Ninol COMF from Stepan Company
(16). EGDS from Golschmidt Chemical Company
(17). Lipopeg 6000 Distearate Lipo Chemical Company
(18). ZPT from Arch Chemical
(19). Zinc Carbonate from Bruggeman Group
(20). Jaguar C500 from Rhodia with a M. Wt of 500,000 g/mol and charge density of 0.8 meq/g
(21). Polyquaternium-10 JR 30M
(22). Poly (Dially) Dimethyl Ammonium Chloride Sourced by Rhodia
(23). A blend from Ashland, which is a blend of 95:5 guar hydroxypropyltrimonium chloride (M. Wt 500,000 g/mol; charge density 1.1 meq/g to AM/APTAC (M. Wt 1,100,000 g/mol; charge density 1.8 meq/g
(24). CO 1895 from Procter & Gamble
(25). CO 1695 from Procter & Gamble
(26). Hydrochloric Acid (pH adjustment)
(27). Kathon CG from Akzo Nobel (Preservative)
(28). Sodium Chloride (QS viscosity adjustment)
(29). Sodium Xylene Sulfonate (QS viscosity adjustment)
(30). Sodium Benzoate (Preservative)
(31). Water (QS)

TABLE 7

| Shampoo Examples | | | | | | | | | | | | | |
|---|---|---|---|---|---|---|---|---|---|---|---|---|---|
| | Example Compositions | | | | | | | | | | | | |
| | 39 | 40 | 41 | 42 | 43 | 44 | 45 | 46 | 47 | 48 | 49 | 50 | 51 |
| Water and Minors (QS to 100%) | QS | QS | QS | QS | QS | QS | QS | QS | QS | QS | QS | QS | QS |
| Sodium Laureth Sulfate (1) | 16 | 16 | 16 | 16 | 16 | 15 | 15 | 15 | 15 | 15 | 15 | 15 | 15 |
| Cocamidopropyl Betaine (2) | 1.7 | 1.7 | 1.7 | 1.7 | 1.7 | 1.7 | 1.7 | 1.7 | 1.7 | 1.7 | 1.7 | 1.7 | 1.7 |
| HY-3050 Emulsion (3) | 5.0 | | | | | 7.5 | | 5.0 | | | | | |
| HY-3051 Emulsion (4) | | 2.5 | | | | | 2.5 | | 2.5 | | | | 2.5 |
| Sefose Emulsion (5) | | | 5.0 | | | | | | | | 2.5 | | 2.5 |

TABLE 7-continued

Shampoo Examples

| | Example Compositions | | | | | | | | | | | | |
|---|---|---|---|---|---|---|---|---|---|---|---|---|
| | 39 | 40 | 41 | 42 | 43 | 44 | 45 | 46 | 47 | 48 | 49 | 50 | 51 |
| Soybean oil emulsion (6) | | | | 2.5 | | | | | | | 2.5 | | |
| Hydrogenated soybean oil emulsion (7) | | | | | 2.5 | | | | | | | 2.5 | |
| Guar Hyrdroxypropyltrimonium Chloride (LMW) (8) | | | | | | 0.3 | 0.3 | | | | | | |
| Guar Hyrdroxypropyltrimonium Chloride (HMW) (9) | 0.325 | 0.325 | 0.325 | 0.325 | 0.325 | | | 0.15 | 0.15 | 0.15 | 0.15 | 0.15 | 0.15 |
| Polyquaternium-10 (HMW) (10) | 0.075 | 0.075 | 0.075 | 0.075 | 0.075 | | | | | | | | |
| Poly(Dially)Dimethyl Ammonium Chloride (11) | 0.075 | 0.075 | 0.075 | 0.075 | 0.075 | | | 0.10 | 0.10 | 0.10 | 0.10 | 0.10 | 0.10 |
| Trihydroxystearin (12) | 0.1 | 0.1 | 0.1 | 0.1 | 0.1 | 0.1 | 0.1 | 0.1 | 0.1 | 0.1 | 0.1 | 0.1 | 0.1 |
| Gel Network (13) | 1.0 | 1.0 | 1.0 | 1.0 | 1.0 | 1.0 | 1.0 | 0.5 | 0.5 | 0.5 | 0.5 | 0.5 | 0.5 |
| Glycerin (14) | 0.5 | 0.5 | 0.5 | 0.5 | 0.5 | 0.5 | 0.5 | 0.25 | 0.25 | 0.25 | 0.25 | 0.25 | 0.25 |
| Fragrance | 1.0 | 1.0 | 1.0 | 1.0 | 1.0 | 1.0 | 1.0 | 1.0 | 1.0 | 1.0 | 1.0 | 1.0 | 1.0 |
| Preservatives, pH, viscosity adjustment | Up to 4% | Up to 4% | Up to 4% | Up to 4% | Up to 4% | Up to 4% | Up to 4% | Up to 4% | Up to 4% | Up to 4% | Up to 4% | Up to 4% | Up to 4% |

(15). Sodium Laureth-1 Sulfate from the Stepan Company
(16). Amphosol HCA from Stepan Company
(17). Emulsion Ex. 1
(18). Emulsion Ex. 2
(19). Emulsion Ex. 3
(20). Emulsion Ex. 7
(21). Emulsion Ex. 8
(22). NHance™ BF-17 from Ashland with a MW of 800,000 g/mol and charge density of 1.4 meq/g
(23). NHance™ 3196 from Ashland with a MW of 1,700,000 g/mol and charge density of 0.7 meq/g
(24). PQ-10, KG-30M from Ashland
(25). PQ-6 from Rhodia
(26). Thixcin® R from Elementis
(27). Gel Network, Table 1
(28). Glycerin from P&G

TABLE 8

Body wash Examples

| Composition | 52 | 53 | 54 | 55 |
|---|---|---|---|---|
| Cleansing phase, % | | | | |
| Distilled Water | Q.S. | Q.S. | Q.S. | Q.S. |
| Sodium Tridecyl Ether Sulfate | 12.6 | 12.6 | 12.6 | 12.6 |
| Laurylamidopropyl Betaine | 7.67 | 7.67 | 7.67 | 7.67 |
| Sodium Chloride | 4.75 | 4.75 | 4.75 | 4.75 |
| Iconol TDA3-Ethoxylated Tridecyl Alcohol | 1.40 | 1.40 | 1.40 | 1.40 |
| N-Hance CG17 Cationic Guar | 0.42 | 0.42 | 0.42 | 0.42 |
| Preservative 1 | 0.28 | 0.28 | 0.28 | 0.28 |
| Preservative 2 | 0.037 | 0.037 | 0.037 | 0.037 |
| Associative Polymer | 0.15 | 0.15 | 0.15 | 0.15 |
| Sequestering agent | 0.15 | 0.15 | 0.15 | 0.15 |
| Oxidizer (50% solution) | 0.07 | 0.07 | 0.07 | 0.07 |
| Benefit phase, % | | | | |
| Emulsion (Ex. 3) | 2.5-25 | — | — | — |
| Emulsion (Ex. 1) | — | 2.5-25 | — | — |
| Emulsion (Ex. 5) | — | — | 2.5-25 | — |
| Emulson (Ex. 2) | — | — | — | 2.5-25 |

Wet and Dry Conditioning Tests

Using the abovementioned test protocol on low lift hair, the wet and dry combing benefits of shampoo formulations containing soy oligomer and sucrose polyester emulsions were measured on different hair types

TABLE 9

| Shampoo Formulation | Benefit Agent | Mean |
|---|---|---|
| Comp. Example 1 | — | 2.50 |
| Example 2 | 0.5% HY-3051 | 5.25 |
| Example 4 | 1.0% Sefose 8/85 | 6.50 |
| Example 3 | 0.5% Sefose 8/85 | 5.06 |

As the data shows, soy oligomer and sucrose polyester emulsions provide consumer noticeable benefits in both the wet and dry state and across hair type.

TABLE 10

| Damaged hair switches (6 inches in length) treated with composition 5 times | Water contact angle (degree) | |
|---|---|---|
| | Near tip of hair switch | In middle of hair switch |
| Inventive Ex. 3 | 80 | 67 |
| Comparitive Ex. 7 | 59 | 55 |

As data shows, soy oligomer pre-emulsion provide benefit of modifying the damages hair surface energy toward more hydrophobic conditions.

Panelists were give one composition product and a commercial conditioner to use in shower for one week. The commercial conditioner is same for all panelists and all composition. Compositions are randomized for usage sequence among all panelists. Panelists wrote diaries after each use and fill out questionaires. At end of each week, the panelists were interviewed.

% of panelists that preferred the compositions is calculated as: Number of panelists who prefer a composition vs. Ex. 7*100%/total number of panelists (n=8). For example: 5 panelist preferred Ex. 5 over Ex. 7, 5*100%/8=63%

TABLE 11

| Shampoo composition | % of panelists (n = 8) that preferred composition vs. Ex. 7 |
|---|---|
| Ex. 3 | 100 |
| Ex. 5 | 63 |

The positive verbatim of benefits include:
"smooth satin feel""
"smooth look with every hair in its place"
"hair looks healthy and natural, volumizing, soft, thick and moisturized hair feel and fast drying."

The personal care composition may be presented in typical hair care formulations. They may be in the form of solutions, dispersion, emulsions, powders, talcs, encapsulated spheres, spongers, solid dosage forms, foams, and other delivery mechanisms. The compositions of the embodiments of the present invention may be hair tonics, leave-on hair products such as treatment and styling products, rinse-off hair products such as shampoos, and any other form that may be applied to hair.

The personal care compositions are generally prepared by conventional methods such as those known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) from about 0.25% to about 80% of a pre-emulsified emulsion comprising from about 0.005% to about 80% of one or more materials selected from the group consisting of metathesized unsaturated polyol esters, and fatty esters with a molecular weight greater than or equal to 1500 and mixtures thereof;
   wherein an emulsifier is selected from the group consisting of anionic, non-ionic, cationic, amphoteric and mixtures thereof wherein the average particle size of the pre-emulsified emulsion is from about 20 nanometers to 20 microns;
   b) from about 5% to about 50% of one or more anionic surfactants, by weight of said personal care composition;
   c) at least about 20% of an aqueous carrier, by weight of said personal care composition
   wherein the composition is stable with respect to one of the following measures selected from emulsion particle size, viscosity or visual phase separation and mixtures thereof.

2. The personal care composition of claim 1 wherein the average particle size of the pre-emulsified emulsion is from about 100 nm to 20 microns.

3. The personal care composition of claim 1 wherein the average particle size of the metathesized unsaturated polyol esters, or fatty esters in the hair care composition is from about 100 nm to 20 microns.

4. The personal care composition of claim 1 wherein the aqueous carrier is a water-miscible solvent.

5. The personal care composition of claim 1, wherein the preemulsion comprise 0.25% to 50% of metathesized unsaturated polyol esters, or fatty esters or mixtures therefore.

6. The personal care composition of claim 1, wherein one or more oligomers are derived from metathesis of unsaturated polyol esters and further wherein said one or more oligomers is a triglyceride oligomer.

7. The personal care composition of claim 6, wherein said triglyceride oligomer is a soy oligomer.

8. The personal care composition of claim 7, wherein said soy oligomer is fully hydrogenated.

9. The personal care composition of claim 7, wherein said soy oligomer is about 80% hydrogenated or more.

10. The personal care composition of claim 7 wherein said soy oligomer is about 80% non-hydrogenated or more.

11. The personal care composition of claim 1, wherein said one or more anionic surfactants is sodium laureth sulfate.

12. The personal care composition of claim 1, further comprising from about 0.02% to about 0.5% of a cationic polymer, by weight of said personal care composition.

13. The personal care composition of claim 1, wherein said hair care composition further comprises one or more additional conditioning agents.

14. The personal care composition of claim 13, wherein said one or more additional conditioning agents is a silicone.

15. The personal care composition of claim 1, wherein said personal care composition further comprises one or more additional benefit agents.

16. The personal care composition of claim 15, wherein said one or more additional benefit agents is selected from the group consisting of anti-dandruff agents, vitamins, chelants, perfumes, brighteners, enzymes, sensates, attractants, anti-bacterial agents, dyes, pigments, bleaches, and mixtures thereof.

17. The personal care composition of claim 16 wherein the anti dandruff agent is a polyvalent metal salt of pyrithione.

18. The personal care composition of claim 17 wherein the anti-dandruff agent is zinc pyrithione.

19. The personal care composition of claim 1 wherein said personal care composition further comprises a zinc-containing layered material.

20. The personal care composition of claim 19 wherein the zinc-containing layered material is basic zinc carbonate.

21. The personal care composition of claim 1, further comprising a dispersed gel network phase comprising:
   a. at least about 0.05% of one or more fatty alcohols, by weight of said hair care composition;
   b. at least about 0.01% of one or more gel network surfactants, by weight of said hair care composition; and
   c. water.

22. The personal care composition of claim 1, wherein one or more oligomers are derived from metathesis of unsaturated polyol esters and further wherein said one or more oligomers are self-metathesized.

23. The personal care composition of claim 1, wherein one or more oligomers are derived from metathesis of unsaturated polyol esters and further wherein said one or more oligomers are cross-metathesized.

24. The personal care composition of claim 1, wherein said hair care composition further comprises one or more non-metathesized unsaturated polyol esters.

25. The personal care composition of claim 24, wherein said one or more non-metathesized unsaturated polyol esters includes a soy bean oil and other natural oils.

26. A method for cleansing hair comprising the step of applying an effective amount of the personal care composition of claim 1 to the hair.

27. The personal composition of claim 1 wherein there is an increase deposition of silicone when in combination with materials selected from the group consisting of metathesized unsaturated polyol esters, and fatty esters with a molecular weight greater than or equal to 1500 and mixtures thereof.

* * * * *